(12) United States Patent
Scheland

(10) Patent No.: US 8,784,498 B2
(45) Date of Patent: Jul. 22, 2014

(54) METHOD AND APPARATUS FOR FUSING THE BONES OF A JOINT

(76) Inventor: John Scheland, Old Forge, PA (US)

(*) Notice: Subject to any disclaimer, the term of this patent is extended or adjusted under 35 U.S.C. 154(b) by 247 days.

(21) Appl. No.: 12/982,404

(22) Filed: Dec. 30, 2010

(65) Prior Publication Data

US 2011/0172780 A1    Jul. 14, 2011

Related U.S. Application Data

(60) Provisional application No. 61/335,100, filed on Dec. 31, 2009.

(51) Int. Cl.
*A61F 2/42* (2006.01)

(52) U.S. Cl.
USPC ..................... 623/21.11; 623/18.11

(58) Field of Classification Search
USPC ............. 623/17.16, 21.11, 21.19, 18.11
See application file for complete search history.

(56) References Cited

U.S. PATENT DOCUMENTS

| | | | |
|---|---|---|---|
| 7,172,627 | B2 | 2/2007 | Fiere et al. |
| 7,594,931 | B2 | 9/2009 | Louis et al. |
| 2004/0176852 | A1 | 9/2004 | Zubok et al. |
| 2007/0198016 | A1 | 8/2007 | Zang et al. |

*Primary Examiner* — Bruce E Snow
(74) *Attorney, Agent, or Firm* — Pandiscio & Pandiscio

(57) ABSTRACT

Apparatus for fusing a first bone of a joint with a second bone of a joint, the apparatus comprising:
  a fusion block comprising a hollow tubular structure characterized by a first end, a second end and a lumen extending from said first end to said second end, the first end being configured to engage the first bone of the joint and the second end being configured to engage the second bone of the joint, the lumen being configured to span the distance from the first bone of the joint to the second bone of the joint and to receive and retain bone graft material therein, whereby to facilitate bone fusion across the fusion block; and
  at least one fusion plate for connecting the fusion block to the first bone of the joint and the second bone of the joint.

11 Claims, 39 Drawing Sheets

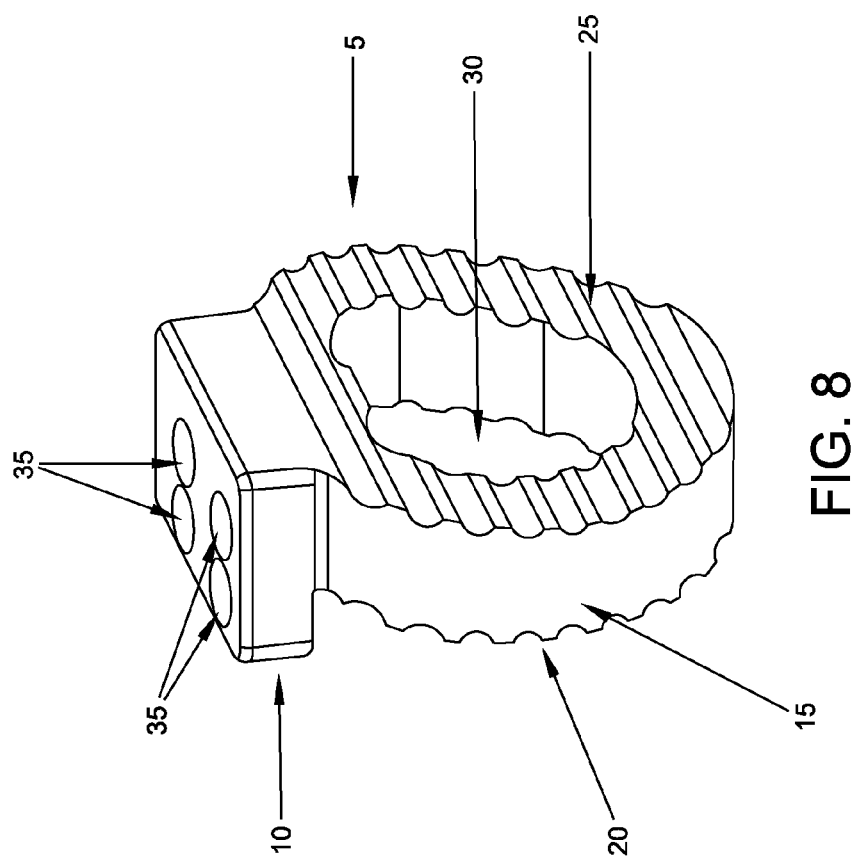

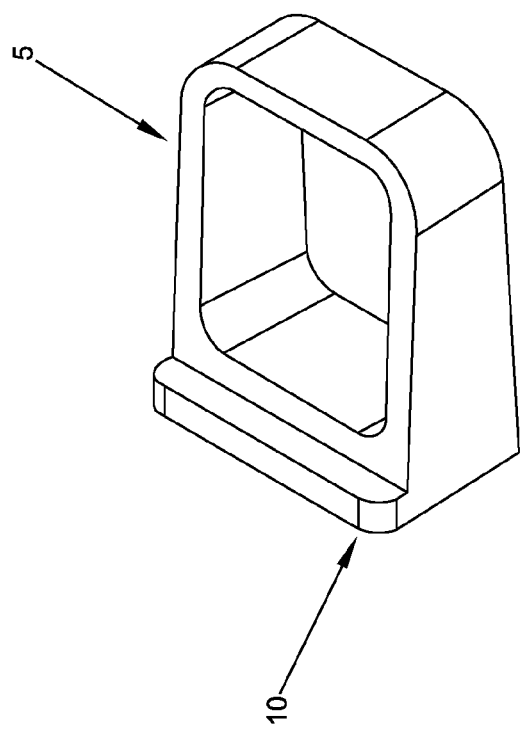
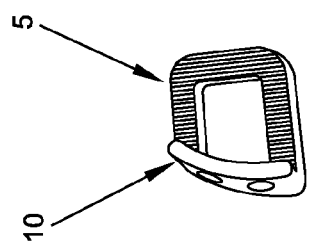

METHOD AND APPARATUS FOR FUSING THE BONES OF A JOINT

REFERENCE TO PENDING PRIOR PATENT APPLICATION

This patent application claims benefit of pending prior U.S. Provisional Patent Application Ser. No. 61/335,100, filed Dec. 31, 2009 by John Scheland et al. for BONE FUSION SYSTEM FOR EXTREMITIES, which patent application is hereby incorporated herein by reference.

FIELD OF THE INVENTION

This patent application relates to surgical methods and apparatus in general, and more particularly to surgical methods and apparatus for fusing the bones of a joint.

BACKGROUND OF THE INVENTION

The joints in the limbs of a human are frequently subject to a loss of function due to trauma and/or disease. As these joints become increasingly more painful and problematic for the patient, surgeons generally have relatively few options for restoring the form and function of the affected joints. In addition, many clinical factors (including but not limited to patient age, patient weight and general patient health) further complicate the task of restoring the affected joints to a fully functional, pain-free condition. In this respect it should also be appreciated that the smaller joints of the limbs are characterized by wide variations in topography, and impose substantial size constraints, which can make restoring an affected joint to pain-free mobility difficult or impossible.

Arthrodesis

The standard treatment for end stage arthrosis in the foot and wrist is a resectional arthrodesis. This is achieved by resecting the articular cartilage and subchondral bone of the joint. Without interpositional bone grafting of a resectional arthrodesis, the fusion will require that the bone ends be brought together and stabilized. Arthrodesis of this nature can be difficult to perform. This is because the small bones in the foot and wrist are surrounded by many odd-shaped bones, with multiple ligamentous attachments, thus creating significant difficulty in achieving end-to-end contact. To bring these bones together typically requires, among other things: extensive dissection of the surrounding ligaments to mobilize the bones; the use of high-angle interfragmentary screws, which often results in screw pull-out and unintended bone fracture; and plate fixation, which often results in increased unnecessary compressive loading of the screws, thereby resulting in hardware failure. Furthermore, when arthrodesis is achieved without interpositional bone grafting, the area of fusion becomes shorter, resulting in iatrogenic deformity.

Open-Wedge Osteotomy

The open-wedge osteotomy (OWO) is an indispensable tool in the correction of many deformities. In the case of the foot, the most common osteotomies utilizing this method are in the first metatarsal to correct primus varus deformity, and in the calcaneal neck to correct flatfoot deformity (Evans osteotomy).

The first metatarsal open-wedge osteotomy is utilized to correct primus varus deformity when other options would result in an unacceptable shortening of the first metatarsal. Present techniques require interpositional grafting where primary stabilization (by directly fixating the graft into the osteotomy) is difficult if not impossible to achieve. This technique is inexact and often results in either over-correction or under-correction. Recently, expensive Darco plates have been developed in an attempt to achieve this goal. These Darco plates contain, in their centers, a metal block spacer to maintain the desired correction. While these Darco plates have improved this procedure, the Darco plates are not completely satisfactory. For one thing, the metal block spacer in the center of the Darco plates does not allow boney integration into the metal block spacer, thus requiring additional bone graft material to be placed into the remaining boney defect. Furthermore, with the Darco plates, the bone graft material is not incarcerated into the boney defect and can migrate out of the osteotomy site during the post-operative period, thereby resulting in non-unions and repeat surgeries. Also, the Darco plates are made out of stainless steel and titanium, which means that the Darco plates are not radiolucent, and hence it is difficult and/or impossible to perform radiographic studies (to evaluate bone healing) during the post-operative period.

The Evans osteotomy is one of the most common procedures used to correct flatfoot deformity. This technique requires an osteotomy of the calcaneal neck followed by distraction, and then maintenance of distraction by interpositional bone graft or bone graft material. Cortical-cancellous bone grafts are most commonly used. These grafts are brittle and often fracture during placement and/or fixation. If the graft is fractured during placement and/or fixation, it is no longer conducive to primary fixation and dorsal migration of the graft commonly occurs, resulting in loss of correction and pain from iatrogenic boney prominences in the foot. Recently, bone graft analogs have been developed and are being used with increasing frequency. These analogs are much stronger than bone grafts and can be drilled for primary fixation. However, these bone graft analogs are prohibitively expensive and have reduced bone healing properties when compared to autogenous bone.

Bone Defects

Bone defects can occur as a result of the resection of bone lesions, the removal of non-healing fractures and the removal of small implants. When bone defects occur, few options are available to the surgeon. Almost universally, the boney defect must be filled with bone graft material. Most optimally, autogenous bone grafts are used, but this limits the surgeon's ability to stabilize the graft to the surrounding bone. In many cases, external fixation is the best option, but this approach has a number of inherent complications (e.g., pin tract infection) which can cause patient morbidity.

Thus there is a need for a new and improved method and apparatus for fusing the bones of a joint so as to provide relief to a patient.

SUMMARY OF THE INVENTION

The present invention provides a new and improved method and apparatus for fusing the bones of a joint so as to provide relief to a patient.

More particularly, the present invention comprises the provision and use of a new and improved bone fusion system for fusing the bones of a joint.

The new and improved bone fusion system of the present invention is adapted to facilitate small bone arthrodesis, open-wedge osteotomies and bone defect healing, as well as other procedures, by maintaining bone position and stability, simplifying dissection and improving fixation at the fusion sites. The new and improved bone fusion system facilitates boney fusions and bone healing by delivering and incarcerating bone graft material at the fusion site. Furthermore, the present invention may be practiced using less invasive techniques so as to minimize soft tissue resection and/or other trauma, reduce vascular compromise and minimize the potential for developing post-operative neuromas.

The new and improved bone fusion system of the present invention comprises fusion blocks and fusion plates. The fusion blocks are hollow tubular structures which are disposed between the opposing bones of the joint which is to be fused, and are provided in a variety of different shapes and sizes so as to, preferably, approximately match the profile of the surrounding bone. The fusion plates are used to secure the fusion blocks to the surrounding bone and/or to one another and, to this end, the fusion plates are also provided in a variety of different shapes and sizes, and include screw holes for securing the fusion plates to the fusion blocks or to the surrounding bone with screws. Bone graft material is disposed within the hollow interior of the fusion blocks so as to facilitate bone fusion across the fusion blocks. In essence, the fusion blocks provide support for the opposing bones of the joint and simultaneously present a graft-filled passageway between the opposing bones of the joint so as to direct fusion across the joint. Preferably the bone graft material is packed into the hollow interior of the fusion blocks just prior to insertion of the fusion blocks into the joint which is to be stabilized. Alternatively, the fusion blocks may include fenestrations so as to allow the bone graft material to be inserted into the fusion blocks after the fusion blocks have been positioned within the joint.

The fusion blocks and fusion plates may be formed as a single integral element, and/or the fusion blocks and fusion plates may be formed as separate elements which are assembled in situ. In this latter case, the fusion blocks also include screw holes for receiving screws passed through the fusion plates, whereby to secure the fusion plates to the fusion blocks. It will be appreciated that where the fusion blocks and fusion plates are adapted to be assembled in situ, they effectively form a modular system for fusing the bones of a joint. This modular system may be configured so as to establish (i) a rigidly fixed connection preventing motion between fusion blocks and fusion plates, and/or (ii) a semi-constrained, or flexible, connection permitting limited and controlled motion between fusion blocks and fusion plates.

The present invention has application to substantially any joint in the human body, but is believed to have particular application to the joints of the extremities, i.e., from the shoulder joint to the metacarpal joints of the fingers, and/or from the hip joint to the metatarsal joints of the toes. The foot, ankle, hand and wrist are believed to be primary applications of the present invention.

In one preferred form of the invention, there is provided apparatus for fusing a first bone of a joint with a second bone of a joint, the apparatus comprising:

a fusion block comprising a hollow tubular structure characterized by a first end, a second end and a lumen extending from said first end to said second end, the first end being configured to engage the first bone of the joint and the second end being configured to engage the second bone of the joint, the lumen being configured to span the distance from the first bone of the joint to the second bone of the joint and to receive and retain bone graft material therein, whereby to facilitate bone fusion across the fusion block; and at least one fusion plate for connecting the fusion block to the first bone of the joint and the second bone of the joint.

In another preferred form of the invention, there is provided a system for fusing a first bone of a joint with a second bone of a joint, the system comprising:

a fusion block comprising a hollow tubular structure characterized by a first end, a second end and a lumen extending from said first end to said second end, the first end being configured to engage the first bone of the joint and the second end being configured to engage the second bone of the joint, the lumen being configured to span the distance from the first bone of the joint to the second bone of the joint and to receive and retain bone graft material therein, whereby to facilitate bone fusion across the fusion block;

bone graft material disposed within the lumen of the fusion block; and at least one fusion plate for connecting the fusion block to the first bone of the joint and the second bone of the joint.

In another preferred form of the invention, there is provided a method for fusing a first bone of a joint with a second bone of a joint, the method comprising:

providing apparatus comprising:

a fusion block comprising a hollow tubular structure characterized by a first end, a second end and a lumen extending from said first end to said second end, the first end being configured to engage the first bone of the joint and the second end being configured to engage the second bone of the joint, the lumen being configured to span the distance from the first bone of the joint to the second bone of the joint and to receive and retain bone graft material therein, whereby to facilitate bone fusion across the fusion block; and at least one fusion plate for connecting the fusion block to the first bone of the joint and the second bone of the joint;

inserting a fusion block between the first bone and the second bone, and inserting bone graft material into the lumen of the fusion block; and securing the fusion block to the first bone and the second bone using the at least one fusion plate.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 1-11 are schematic views showing various fusion blocks and fusion plates, and illustrate how the fusion blocks and fusion plates may be formed as a single integral element, and/or the fusion blocks and fusion plates may be formed as separate elements which are assembled in situ;

FIG. 11A is a schematic view showing two fusion plates being used to secure a fusion block to bone;

FIGS. 40-50 are schematic views showing an integrated ankle bone fusion (ankle-tibiotalar joint) effected in accordance with the present invention.

DETAILED DESCRIPTION OF THE PREFERRED EMBODIMENTS

Figure 1:
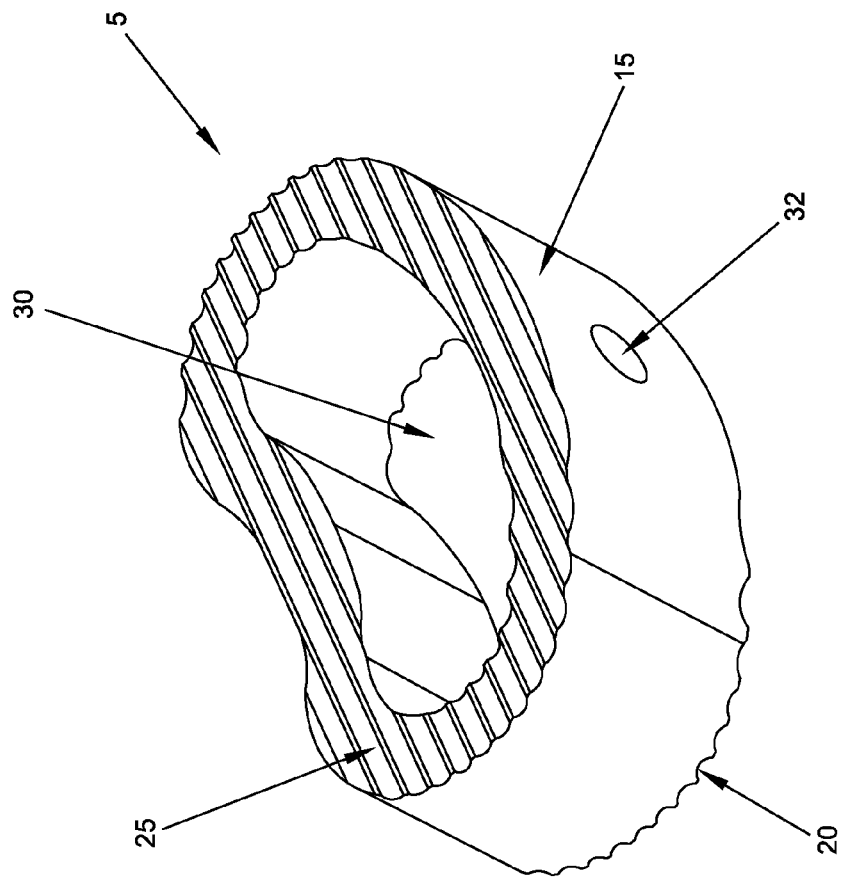
Figure 2:
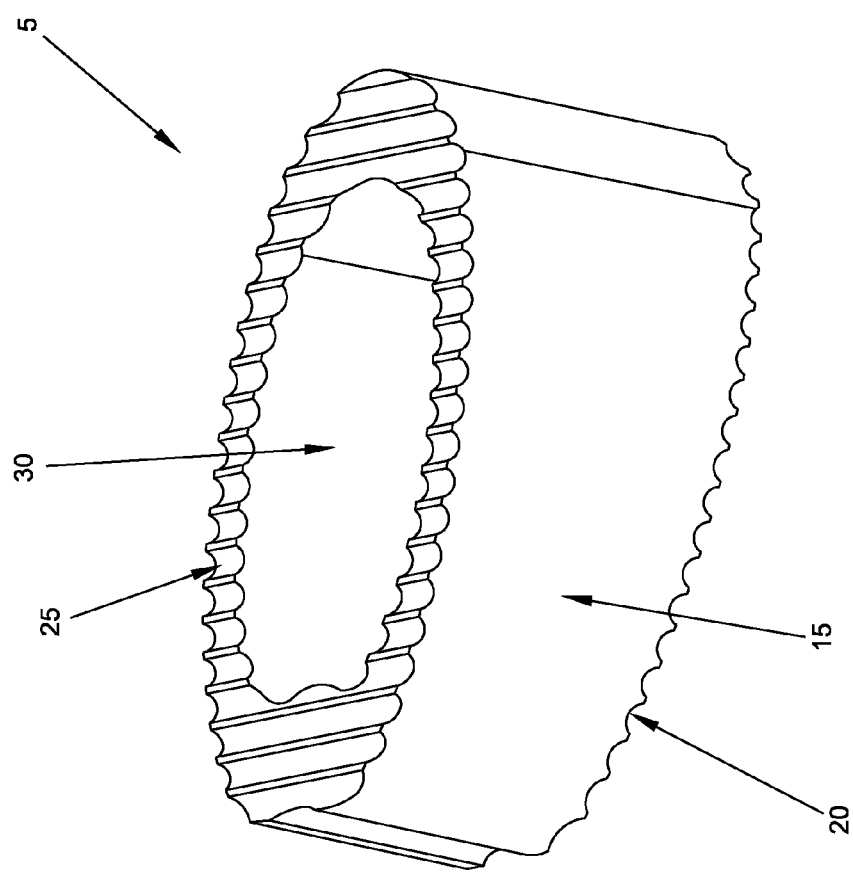
Figure 3:
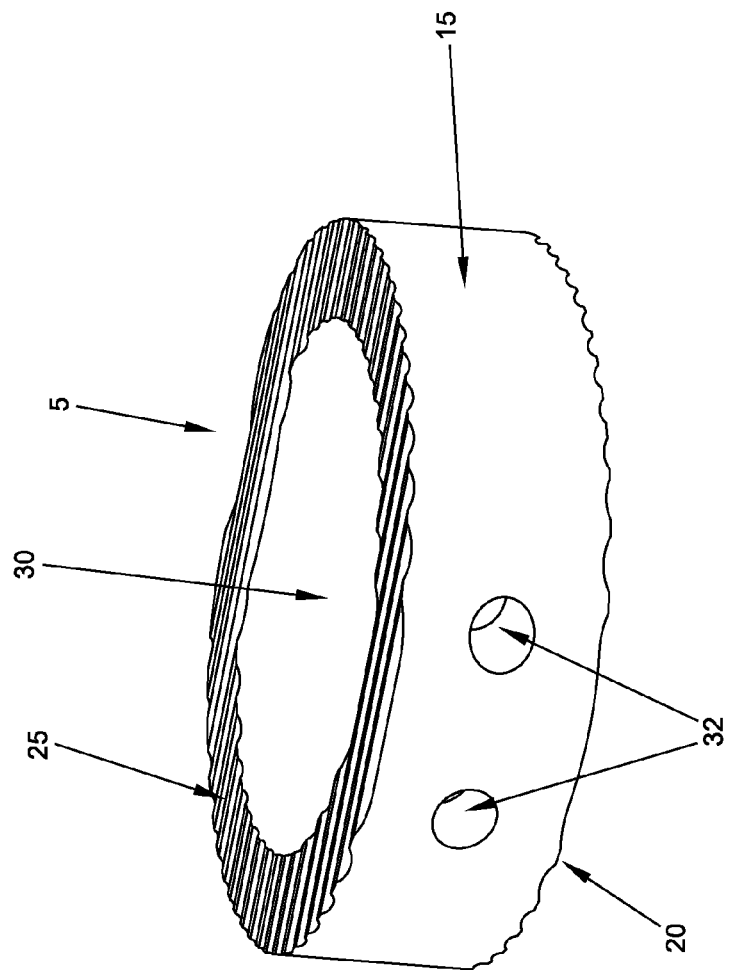
Figure 4:
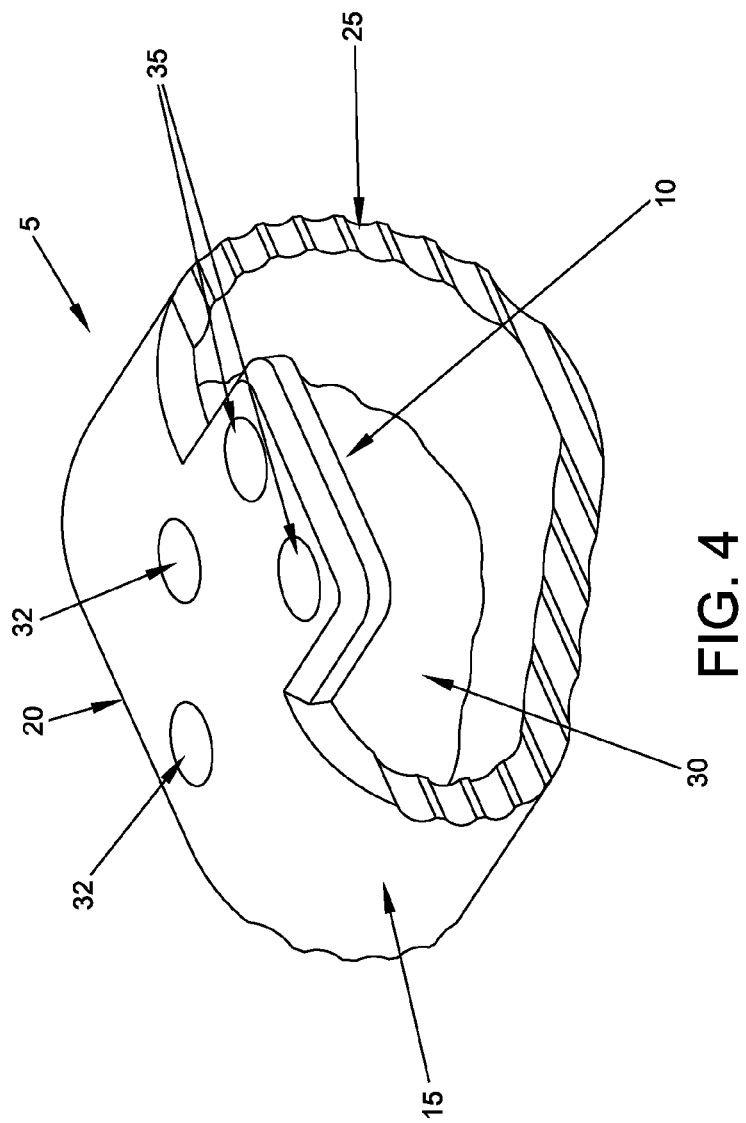
Figure 5:
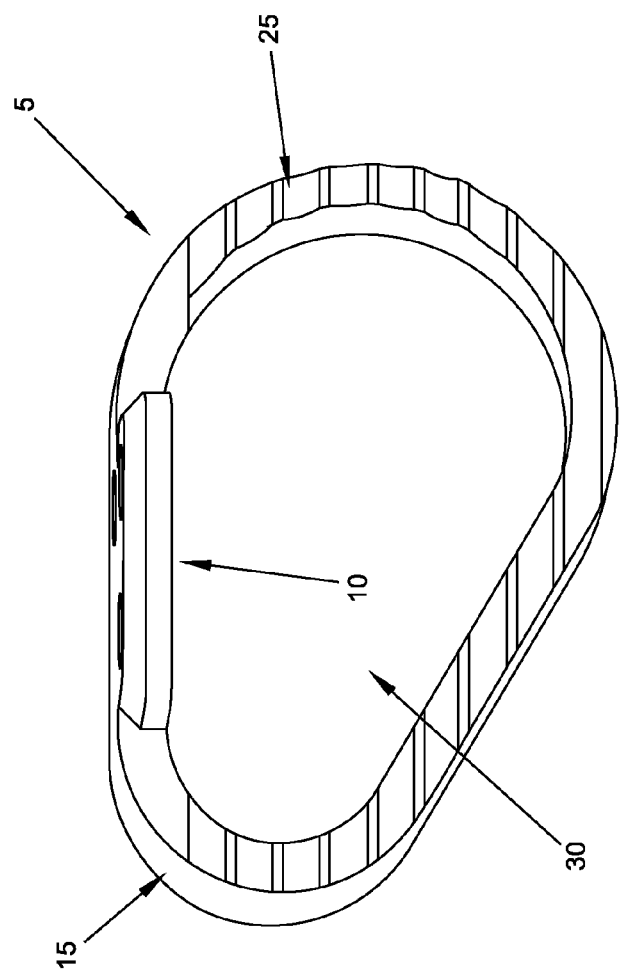
Figure 6:
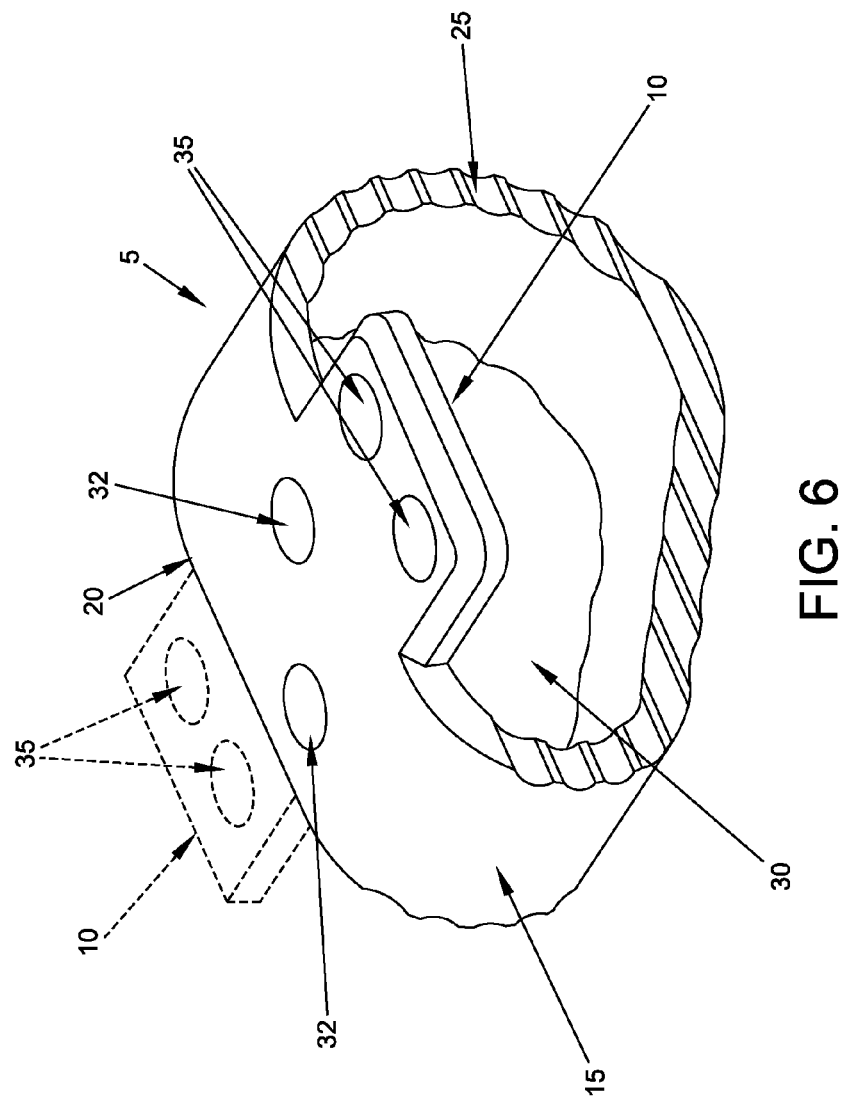
Figure 7:
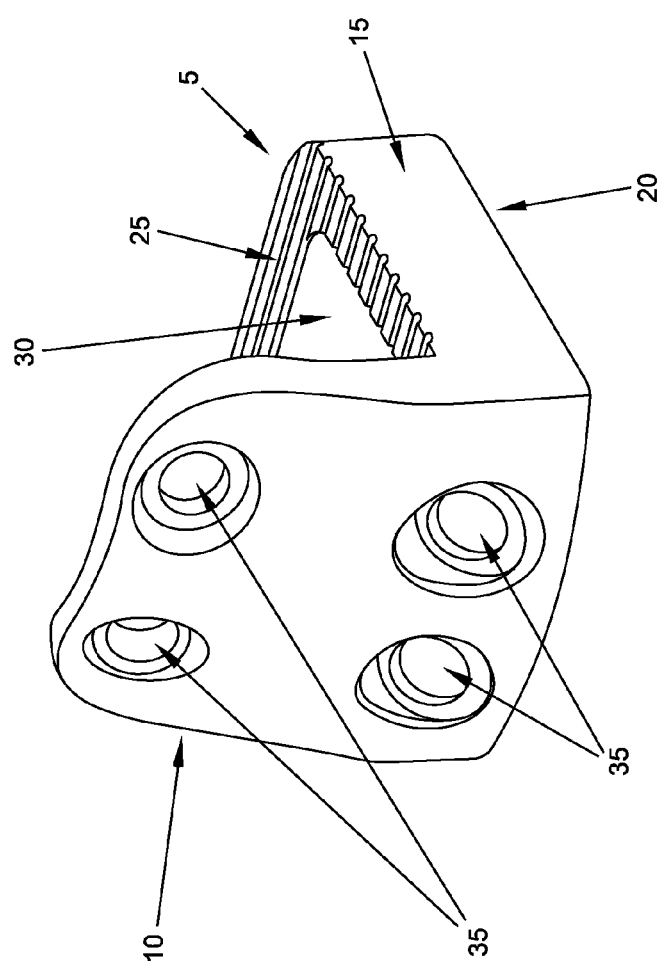
Figure 10:
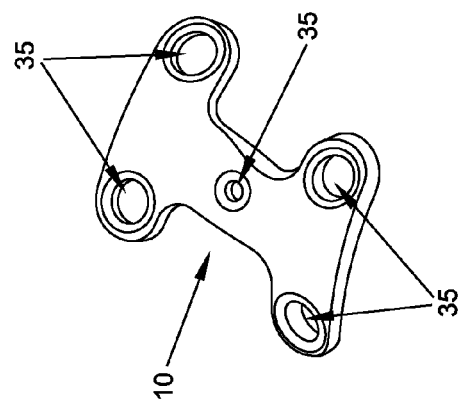
Figure 9:
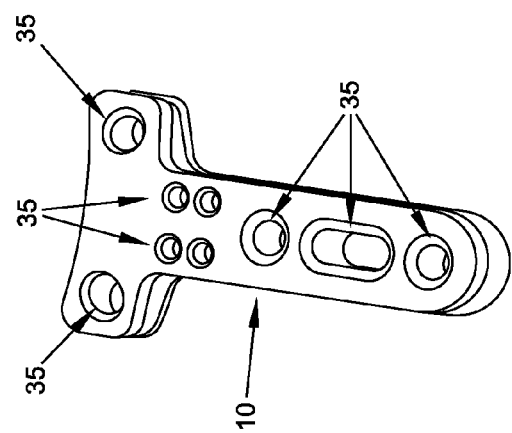

The present invention provides a new and improved method and apparatus for fusing the bones of a joint so as to provide relief to a patient.

More particularly, the present invention comprises the provision and use of a new and improved bone fusion system for fusing the bones of a joint.

The New and Improved Bone Fusion System

The new and improved bone fusion system of the present invention is adapted to facilitate arthrodesis, open-wedge osteotomies and bone defect healing, as well as other procedures, by maintaining boney position and stability, simplifying dissection and improving fixation at the fusion sites. The new and improved bone fusion system facilitates boney fusions and bone healing by delivering and incarcerating bone graft material at the fusion site. Furthermore, the present invention may be practiced using less invasive techniques so as to minimize soft tissue resection and/or other trauma, reduce vascular compromise and minimize the potential for developing post-operative neuromas.

Looking first at FIGS. 1-11, the new and improved bone fusion system of the present invention comprises fusion blocks 5 and fusion plates 10. Fusion blocks 5 are hollow tubular structures which are disposed between the opposing bones of the joint which is to be fused, and are provided in a variety of different shapes and sizes so as to, preferably, approximately match the profile of the surrounding bone. Fusion blocks 5 are generally characterized by a side wall 15 terminating in a first end face 20 and a second end face 25, and defining a hollow interior 30. Fusion blocks 5 preferably also include screw holes 32 for receiving stabilization screws as will hereinafter be discussed. Fusion plates 10 are used to secure the fusion blocks to the surrounding bone and/or to one another and, to this end, the fusion plates are also provided in a variety of different shapes and sizes, and include screw holes 35 for securing the fusion plates to the fusion blocks or to the surrounding bone with screws. Bone graft material is disposed within the hollow interior 30 of fusion blocks 5 so as to facilitate bone fusion across the fusion blocks. In essence, the fusion blocks provide support for the opposing bones of the joint and simultaneously present a graft-filled passageway between the opposing bones of the joint so as to direct fusion across the joint. Preferably the bone graft material is packed into the hollow interior 30 of fusion blocks 5 just prior to insertion of the fusion blocks into the joint which is to be stabilized. Alternatively, fusion blocks 5 may include fenestrations (e.g., screw holes 32, and/or other openings extending through side wall 15 of the fusion blocks) so as to allow the bone graft material to be inserted into the fusion blocks after the fusion blocks have been positioned within the joint.

Figure 11:
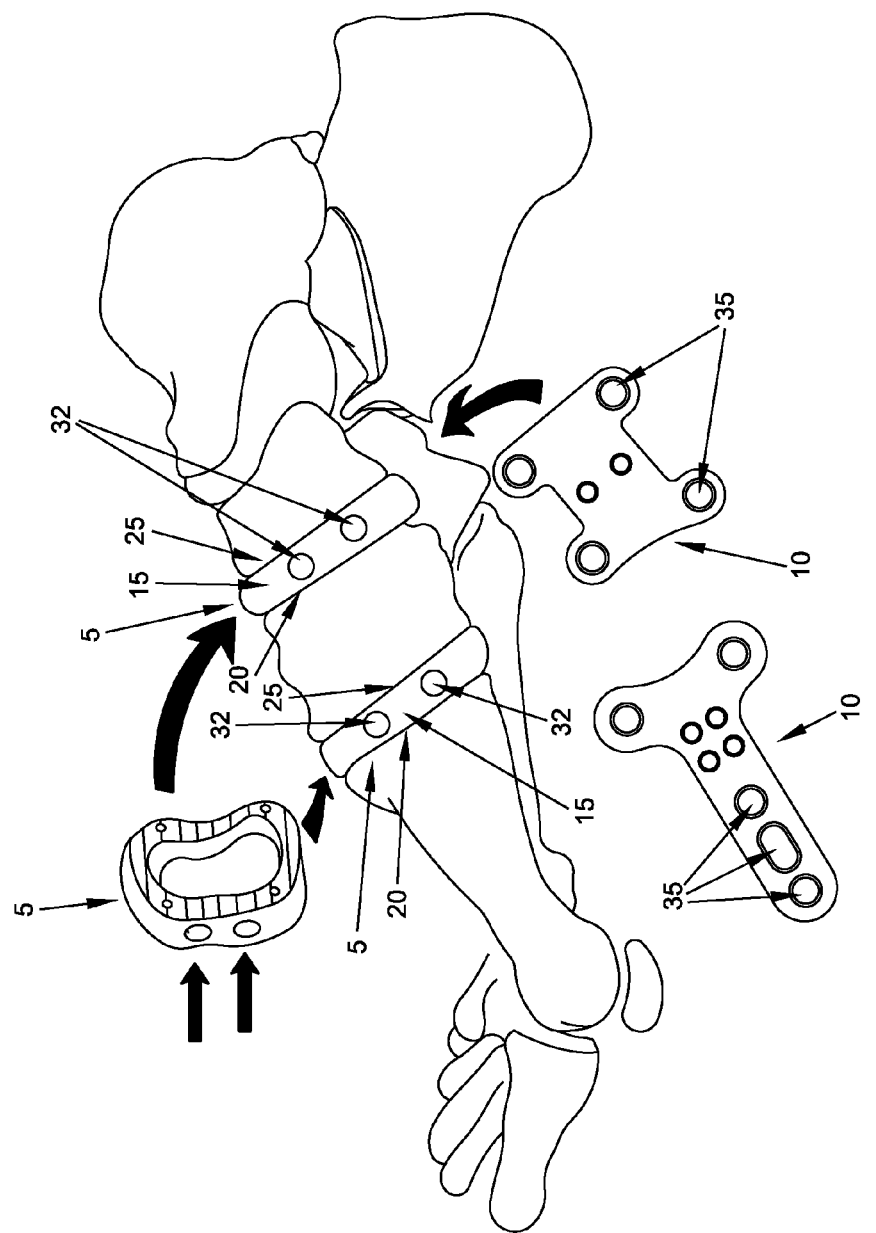

Fusion blocks 5 and fusion plates 10 may be formed as a single integral element (see FIGS. 4-8, including FIG. 6 which shows that a fusion plate 10 can extend out of one and/or both ends of a fusion block 5), and/or fusion blocks 5 and fusion plates 10 may be formed as separate elements (see FIGS. 1-3, 9 and 10) which are assembled in situ (see FIG. 11). In this latter case, fusion blocks 5 also include screw holes 32 for receiving screws passed through fusion plates 10, whereby to secure the fusion plates to the fusion blocks. It will be appreciated that where fusion blocks 5 and fusion plates 10 are adapted to be assembled in situ (see FIGS. 1-3 and 9-11), they effectively form a modular system for fusing the bones of a joint. This modular system may be configured so as to establish (i) a rigidly fixed connection preventing motion between fusion blocks and fusion plates, and/or (ii) a semi-constrained, or flexible, connection permitting limited and controlled motion between fusion blocks and fusion plates. More particularly, where the modular system is configured so as to establish a rigidly fixed connection between fusion blocks 5 and fusion plates 10, screw holes 35 in fusion plates 10 will generally be circular in nature; and where the modular system is configured so as to establish a semi-constrained, or flexible, connection between fusion blocks 5 and fusion plates 10, screw holes 35 in fusion plates 10 will generally be slot-like in nature.

Thus it will be seen that, with the present invention, a fusion block 5, packed with bone graft material, will be stabilized between the opposing bones of a joint via one or more fusion plates 10 and appropriate screws, whereby to effect bone fusion across the joint and thereby provide relief to the patient. Fusion blocks 5 may have fusion plates 10 formed integral therewith, and/or fusion plates 10 may be joined to fusion blocks 5 in situ. A single fusion plate 10 may be formed integral with a single fusion block 5 and be secured to two different bones (and/or to two different fusion blocks, and/or to one bone and one fusion block, etc.). Or a single fusion plate 10 may be formed integral with a single fusion block 5 and be secured to only one bone (or to only one fusion block), in which case a second fusion plate can be used to secure the fusion block to another bone (or to another fusion block). Or a single fusion plate 10 may be formed separate from a single fusion block 5 and be secured to two different bones (and/or to two different fusion blocks, and/or to one bone and one fusion block, etc.), or a single fusion plate 10 may be formed separate from a single fusion block 5 and be secured to only one bone (or to only one other fusion block), in which case a second fusion plate can be used to secure that fusion block to another bone (or to another fusion block). By way of example but not limitation, and looking now at FIG. 11A, two fusion plates 10 may be used to secure a fusion block 5 to bone, with the first fusion plate 10 being attached to a first bone and the second fusion plate 10 being attached to a second bone, wherein the second fusion plate is formed separate from the fusion block 5. It will be appreciated that all of the foregoing arrangements, as well as others, are within the scope of the present invention.

The present invention has application to substantially any joint in the human body, but is believed to have particular application to the joints of the extremities, i.e., from the shoulder joint to the metacarpal joints of the fingers, and/or from the hip joint to the metatarsal joints of the toes. The foot, ankle, hand and wrist are believed to be primary applications of the present invention.

Fusion Blocks. To facilitate the fusion of the bones of a joint, there is provided a series of intra-articular fusion blocks 5 which are configured to fill the unique joint spaces between the previously-articulating bones of a joint. More particularly, fusion blocks 5 are hollow tubular structures which are disposed between the opposing bones of the joint which is to be fused, and come in a variety of different shapes and sizes so as to, preferably, approximately match the profile of the surrounding bone. Fusion blocks 5 are intended to be filled with bone graft material so as to facilitate bone fusion. This is preferably done before the fusion blocks have been positioned within the joint, however, if desired, the fusion blocks may also be provided with fenestrations (e.g., screw holes 32, and/or other openings extending through side wall 15 of the fusion blocks) to allow the bone graft material to be inserted into the interior of the fusion blocks after the fusion blocks have been inserted into the joint. In essence, the fusion blocks provide support for the opposing bones of the joint and simultaneously present a graft-filled passageway between the opposing bones of the joint so as to direct fusion across the joint.

Block Primitives. Fusion blocks 5 can have substantially any size and shape. However, certain sizes and shapes are generally preferred, i.e., the length of the fusion block is preferably substantially equal to the length of cartilage and bone removed from the joint, so as to keep the length of fusion substantially the same length as the native anatomy, and the cross-sectional size of the fusion block is preferably approximately the same as the cross-sectional size of the bones to which it is to abut. Furthermore, certain cross-sectional profiles are generally preferred, and these are oval, kidney, egg, teardrop and distended square.

End Faces. The end faces 20, 25 of fusion blocks 5 can have substantially any configuration. However, certain end face profiles are generally preferred, and these are planar and/or curvilinear. Furthermore, the two end faces 20, 25 of each fusion block 5 may be parallel to one another or inclined relative to one another.

Materials. Fusion blocks 5 may be formed out of substantially any biocompatible materials consistent with the purposes of the present invention. However, certain materials are generally preferred, and these are titanium, titanium alloys, tantalum, PEEK and various stainless steels. PEEK is particularly preferred since it is radiolucent and hence does not interfere with post-operative X-ray evaluation of the bone fusion. In addition, PEEK is also compatible with magnetic resonance imaging (MRI) and hence does not interfere with post-operative MRI evaluation of the bone fusion.

Surface Coatings. To enhance bone in-growth via direct apposition at the bone/fusion block interface, adjunctive biocompatible materials may be applied to the end faces 20, 25 of the fusion blocks. Preferred surface coatings include, but are not limited to, vapor-deposited biocompatible titanium or its alloys, sintered porous coatings, plasma-sprayed titanium and plasma-sprayed biocompatible ceramic coatings.

Fenestrations. Through-holes are preferably formed in the fusion blocks in order to permit easy insertion of bone graft material into the hollow interior of the fusion blocks even after the fusion blocks have been disposed between the opposing bones of the joint, whereby to facilitate bone fusion across the joint. By way of example but not limitation, screw holes 32 may be used to fill the interior of fusion blocks 5 with a bone graft material before a screw is inserted into screw holes 32. Additionally, and/or alternatively, other openings may be provided in the side wall 15 of the fusion blocks so as to allow bone graft material to be inserted into the hollow interiors of the fusion blocks.

Surface Features. To augment the initial stability of fusion block 5 vis-à-vis the adjacent bone, geometric features may be added to the end faces 20, 25 of the fusion blocks so as to improve the stability of the fusion blocks under shear loads across the bone/fusion block interface. These surface features include, but are not limited to, serrations, grooves, dimples, bumps, sintered porous coatings, plasma-sprayed metals and grit-blasted finishes. See, for example, FIGS. 1-8, which show exemplary surface features one or both of the end faces 20, 25.

Fusion Plates. Fusion plates 10 are used to secure fusion blocks 5 to the surrounding bone and/or to one another, e.g., with screws. To this end, fusion plates 10 may be formed in various sizes and in various geometries (e.g., straight, curved, compound shapes, etc.) and be provided with various screw-hole patterns. Fusion plates 10 may be formed integral with fusion blocks 5 (see FIGS. 4-8), and/or formed separate from fusion blocks 5 (see FIGS. 9 and 10), in which case the fusion plates are united with the fusion blocks in situ (see FIG. 11). In this latter case, the fusion blocks and fusion plates effectively form a modular system for fusing the bones of a joint. Fusion plates 10 may be formed out of the same materials as fusion blocks 5 or out of different biocompatible materials. Again, PEEK is a particularly preferred material, since it is compatible with X-ray and MRI apparatus and hence allows good post-operative imaging of bone fusion.

Integral Construction. Forming fusion plates 10 integral with fusion blocks 5 (see FIGS. 4-8) generally provides increased strength and increased stability for the joint fusion, however, it also generally requires the provision of a larger inventory of fusion blocks 5 and fusion plates 10 in order to accommodate a wide range of joint fusions.

Modular System. Forming fusion plates 10 separately from fusion blocks 5 (see FIGS. 1-3 and 9-11) enables various fusion plates to be used with various fusion blocks, thereby increasing the number of intraoperative configurations available to the surgeon and minimizing the inventory which must be kept on hand. The modular system may be configured so as to establish (i) a rigidly fixed connection preventing motion between fusion blocks and fusion plates, and/or (ii) a semi-constrained, or flexible, connection permitting limited and controlled motion between fusion blocks and fusion plates. In this respect it should be appreciated that a modular system providing a rigidly fixed connection between fusion blocks and fusion plates tends to provide a stronger and more stable construct, whereas a modular system providing a semi-constrained, or flexible, connection permits controlled micromotions between the fusion blocks and fusion plates, thereby providing increased bone in-growth and decreasing the level of stress shielding across the joint which is being fused.

Various Configurations. Thus it will be seen that, with the present invention, a fusion block 5, packed with bone graft material, will be stabilized between the opposing bones of a joint via one or more fusion plates 10 and appropriate screws, whereby to effect bone fusion across the joint and thereby provide relief to the patient. Fusion blocks 5 may have fusion plates 10 formed integral therewith, and/or fusion plates 10 may be joined to fusion blocks 5 in situ. A single fusion plate 10 may be formed integral with a single fusion block 5 and be secured to two different bones (and/or to two different fusion blocks, and/or to one bone and one fusion block, etc.). Or a single fusion plate 10 may be formed integral with a single fusion block 5 and be secured to only one bone (or to only one fusion block), in which case a second fusion plate can be used to secure the fusion block to another bone (or to another fusion block). Or a single fusion plate 10 may be formed separate from a single fusion block 5 and be secured to two different bones (and/or to two different fusion blocks, and/or to one bone and one fusion block, etc.), or a single fusion plate 10 may be formed separate from a single fusion block 5 and be secured to only one bone (or to only one other fusion block), in which case a second fusion plate can be used to secure that fusion block to another bone (or to another fusion block). It will be appreciated that all of the foregoing arrangements, as well as others, are within the scope of the present invention.

Bone Graft Material. As noted above, bone graft material is disposed within the interior of the fusion blocks, whereby to promote bone fusion across the fusion blocks. This bone graft material may be bone autograft, allograft or bone substitute materials. In this respect it will be appreciated that, due to the limitations associated with autograft, surgeons are now pursuing the use of ceramic synthetics, bone morphogenic proteins (BMPs), demineralized bone matrices (DBMs) and other allografts, which may be used alone or in combination. In essence, the present invention provides a reservoir depot for bone graft material so as to promote bone fusion across the joint.

In one preferred form of the invention, first end face 20 of fusion block 5 is configured to engage the cortex portion of a first bone of the joint which is to be fused, second end face 25 of fusion block 5 is configured to engage the cortex portion of a second bone of the joint which is to be fused, and the hollow interior 30 of the fusion block is configured to form a passageway between the cancellous portion of the first bone and the cancellous portion of the second bone. As a result, the bone graft material packed into hollow interior 30 of the fusion block provides a direct pathway for bone fusion across the joint.

Use of the New and Improved Bone Fusion System

It will be appreciated that the specific manner of using the new and improved bone fusion system of the present invention will depend to some extent on the specific joint which is to be fused, and on whether the fusion block has a fusion plate formed integral therewith (integrated construction) and/or whether the fusion block is united with one or more fusion plates in situ (modular construction). For this reason, the following description of a preferred manner of using the present invention will be generalized.

In use, the joint which is to be fused is first exposed, taking care to minimize damage to adjacent soft tissue wherever possible. Next, the joint is prepared for fusion, e.g., by distracting the joint, resecting articular cartilage, etc. In the case of small joints of the hand and foot, about 2-3 mm of cartilage/bone is typically removed from each side of the joint. Then an appropriate fusion block 5 is selected, based upon the geometry of the resected joint. In the case of a small joint of the hand and foot, the fusion block will typically have a length of about 4-6 mm, i.e., approximately equal to the length of the resected tissue, so as to maintain the overall length of the native anatomy. The fusion block may or may not have a fusion plate formed integral therewith. Next, the fusion block is filled with bone graft material, and the fusion block is positioned within the joint so that the end faces 20, 25 of the fusion block face the opposing bone. Then the joint is reduced so that the opposing bones of the joint engage the end faces 20, 25 of the fusion block. Next, the fusion block is secured to the opposing bones with screws, either using a fusion plate 10 carried by the fusion block (in which case the screws pass through the fusion plate and into the adjacent bone) and/or with separate fusion plates united with the fusion block in situ (in which case the screws pass through the fusion plate and into the fusion block and/or the adjacent bone). Thereafter, the bone graft material disposed within fusion block 5 facilitates bone fusion across the joint.

Exemplary Applications

The new and improved bone fusion system of the present invention may be used to fuse the bones of substantially any joint in the human body, but is believed to have particular application to the joints of the extremities, e.g., the hands and the feet. For the purposes of example but not limitation, there will hereinafter be disclosed five (5) exemplary fusion applications of the present invention, i.e., three "straight fusion implants" to accommodate specific mid-foot regions (the metatarsal cuneiform bone fusion (medial column), the navicular cuneiform bone fusion (medial column), and the calcaneal cuboid bone fusion (lateral column)); the integrated talar/navicular bone fusion; and the integrated ankle bone fusion.

Figure 12:
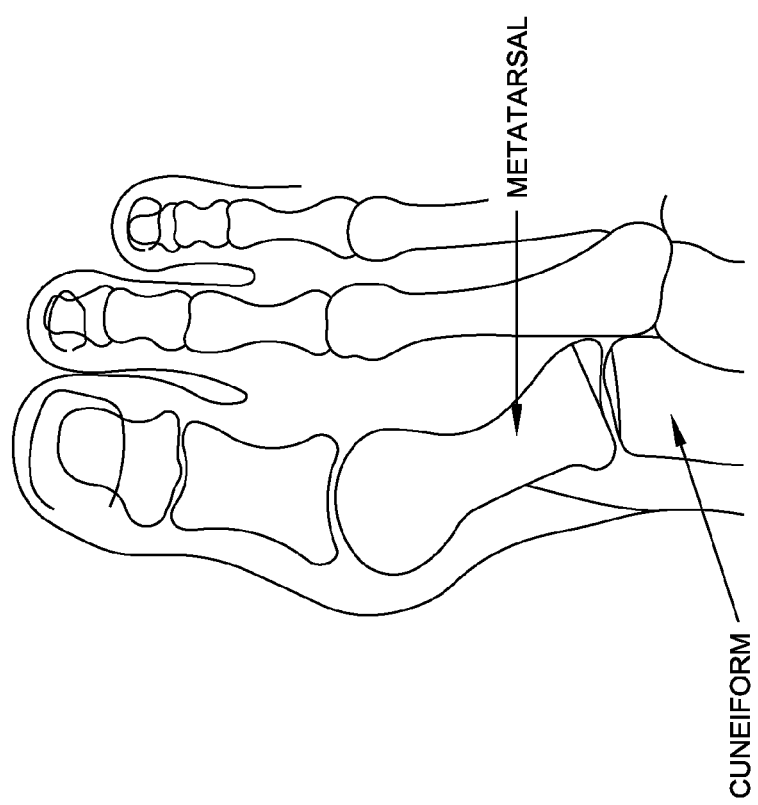
FIGS. 12-18 are schematic views showing a metatarsal cuneiform bone fusion (medial column) effected in accordance with the present invention.
Figure 14:
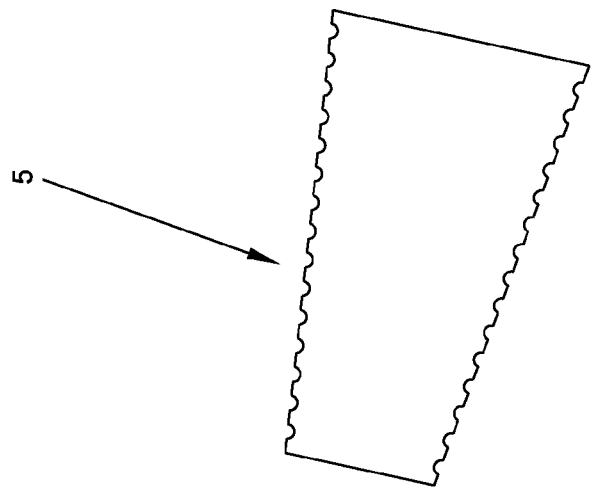
Figure 13:
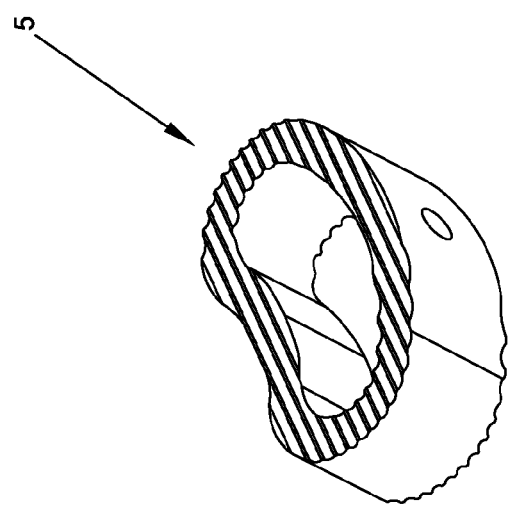
Figure 15:
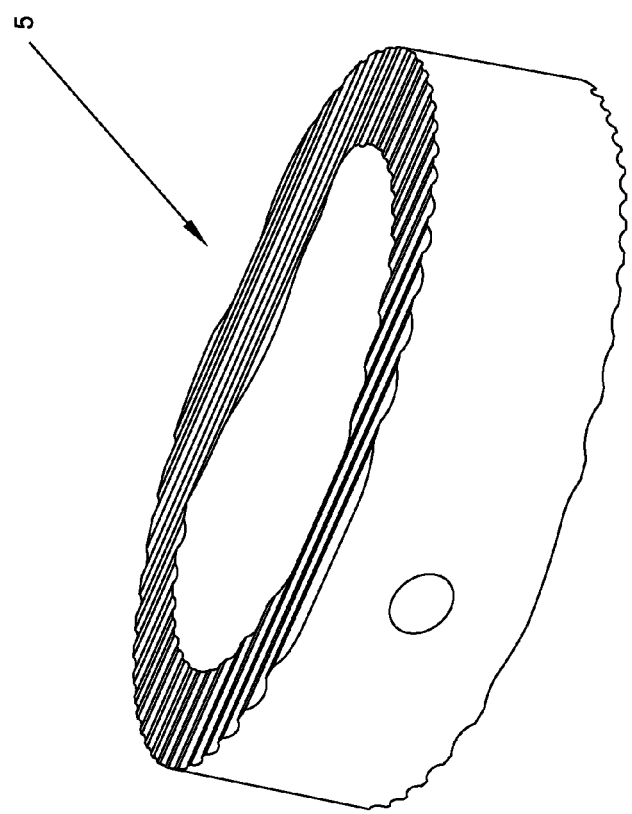
Figure 16:
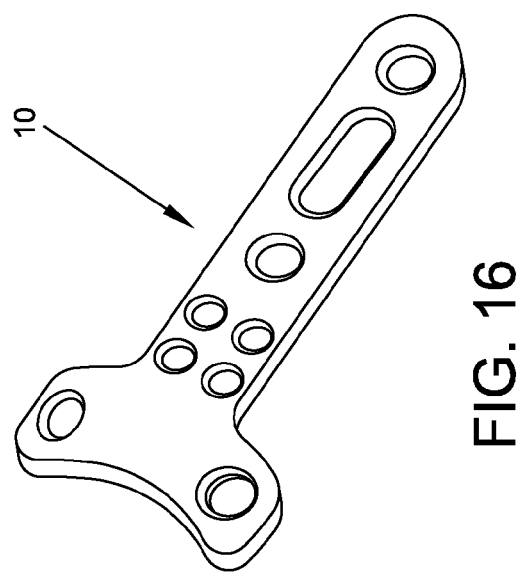
Figure 17:
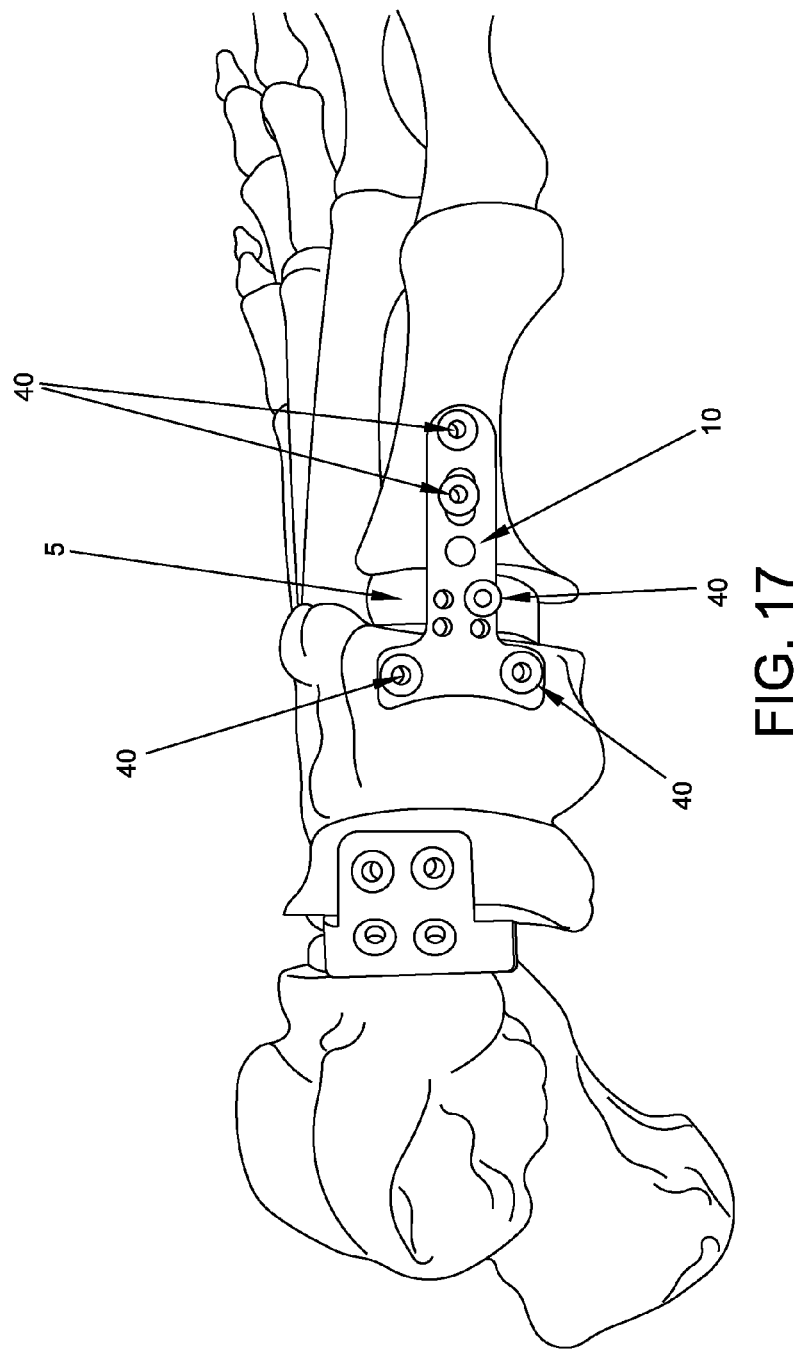
Figure 18:
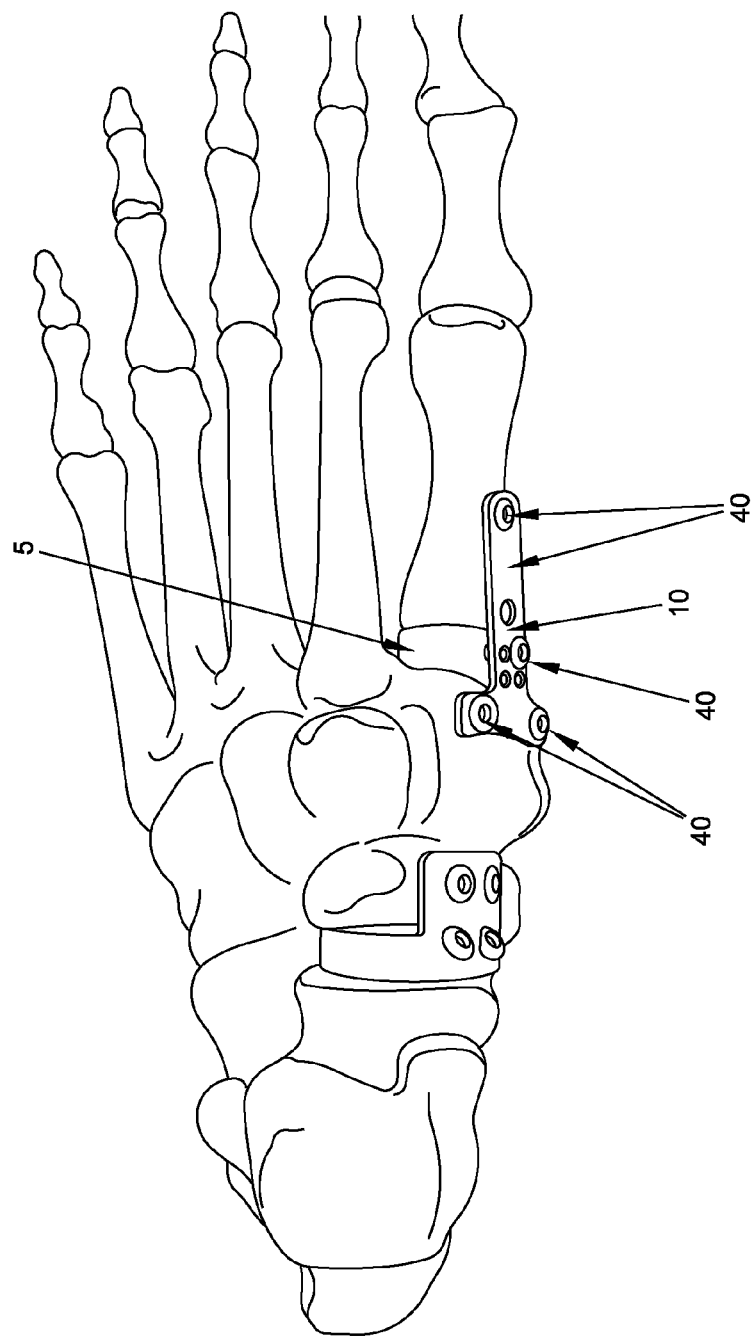

(i) The Metatarsal Cuneiform Bone Fusion (Medial Column) (Kidney-Shaped) (PEEK)—Also Called The "Lapidus Procedure"). This procedure involves arthrodesis of the metatarsal cuneiform joint. The relevant anatomy is shown in FIG. 12. In this bone fusion, the fusion block 5 shown in FIGS. 13-15 is used in conjunction with the fusion plate 10 shown in FIG. 16. As seen in FIGS. 17 and 18, the fusion block 5 is interposed between the first metatarsal and the cuneiform bone, and then the fusion block is secured using fusion plate 10 and screws 40. Note how one of the screws 40 secures fusion plate 10 to fusion block 5 while others of the screws 40 secure fusion plate 10 to adjacent bone.

Figure 19:
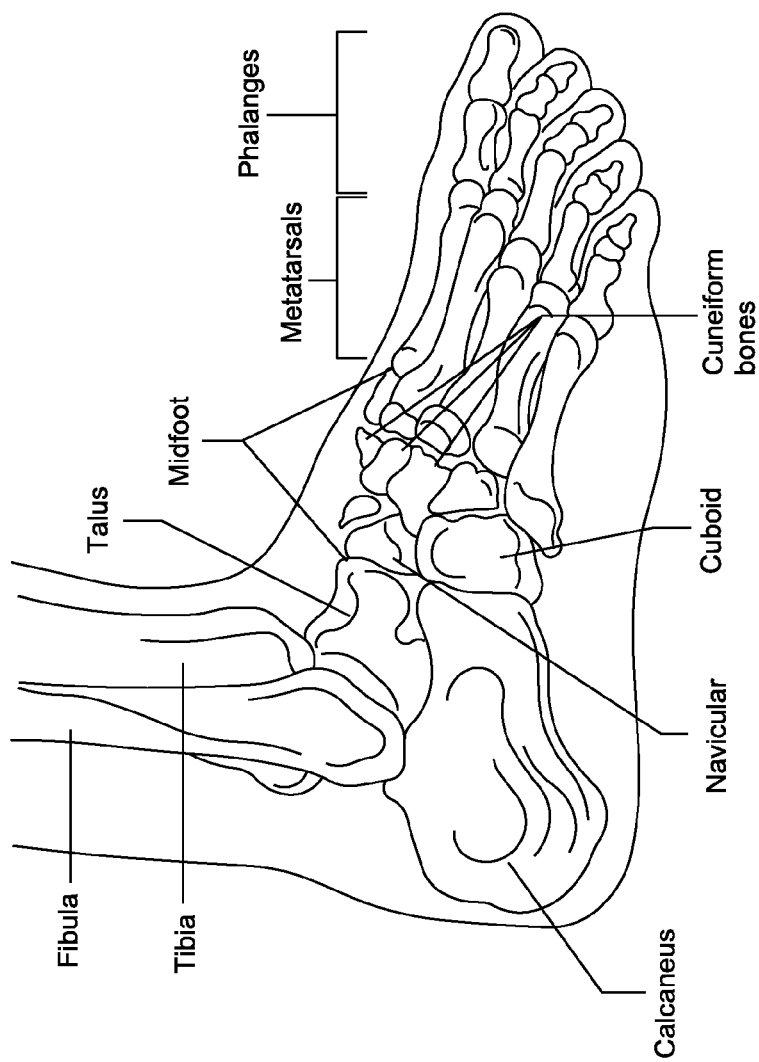
FIGS. 19-22 are schematic views showing a navicular cuneiform bone fusion (medial column) effected in accordance with the present invention.
Figure 20:
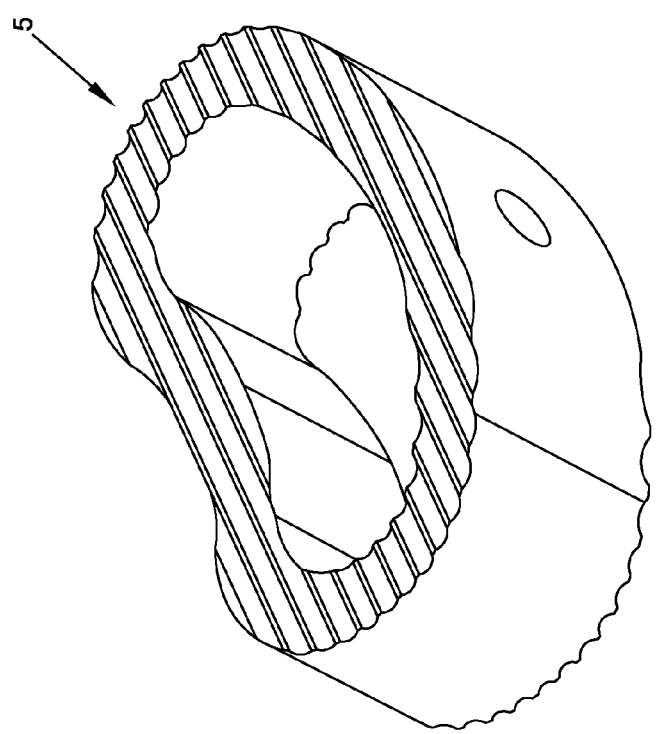
Figure 21:
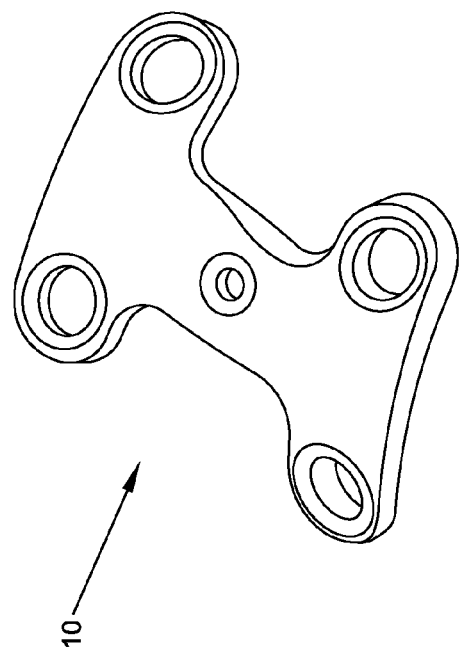
Figure 22:
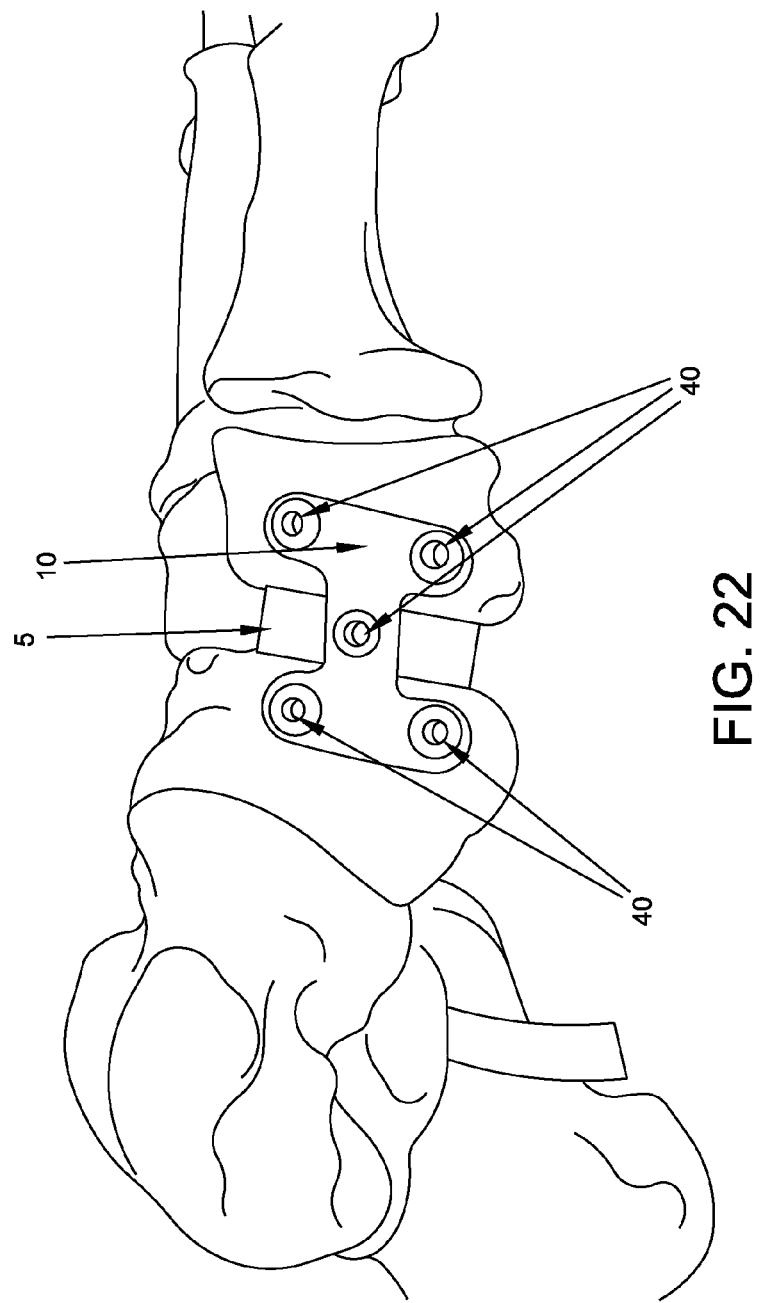

(ii) The Navicular Cuneiform Bone Fusion (Medial Column) (Kidney-Shaped) (PEEK). This procedure involves arthrodesis of the navicular cuneiform joint. The relevant anatomy is shown in FIG. 19. In this bone fusion, the fusion block 5 shown in FIG. 20 is used in conjunction with the fusion plate 10 shown in FIG. 21. As seen in FIG. 22, the fusion block 5 is interposed between the navicular bone and the cuneiform bone, and then the fusion block is secured using fusion plate 10 and screws 40. Again, note how one of the screws 40 secures fusion plate 10 to fusion block 5 while others of the screws 40 secure fusion plate 10 to adjacent bone.

Figure 23:
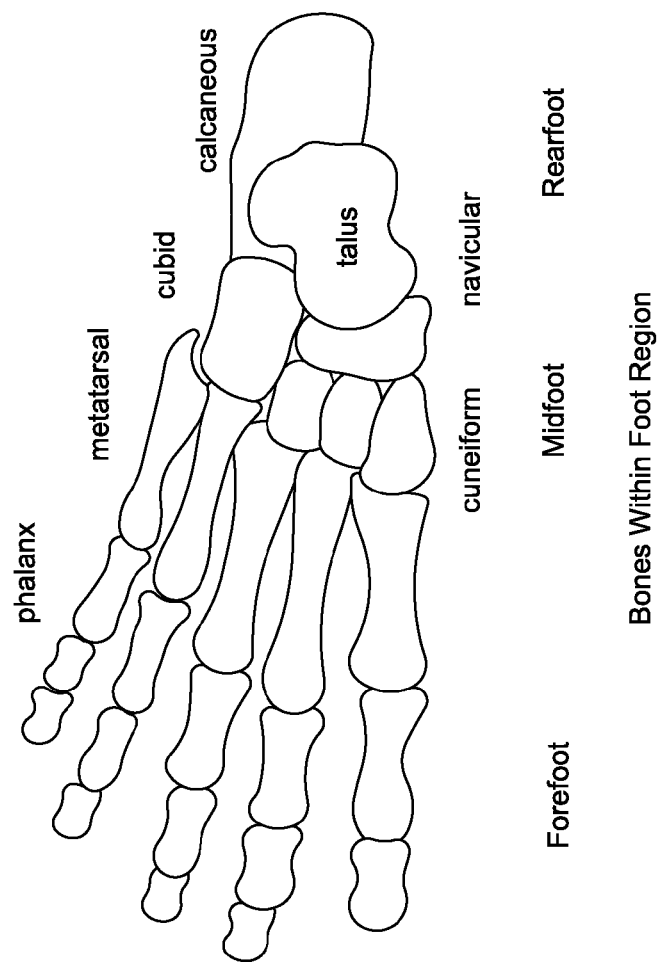
FIGS. 23-30 are schematic views showing a calcaneal cuboid bone fusion (lateral column) effected in accordance with the present invention.
Figure 25:
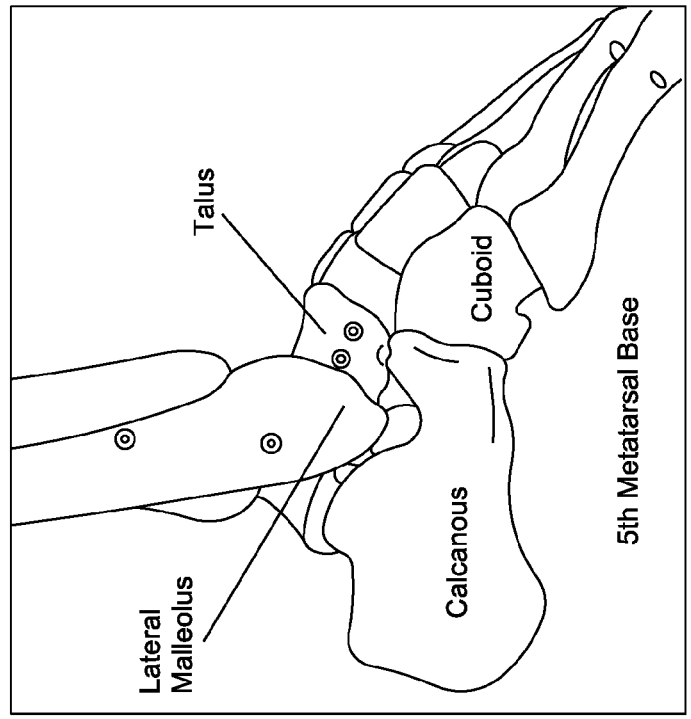
Figure 24:
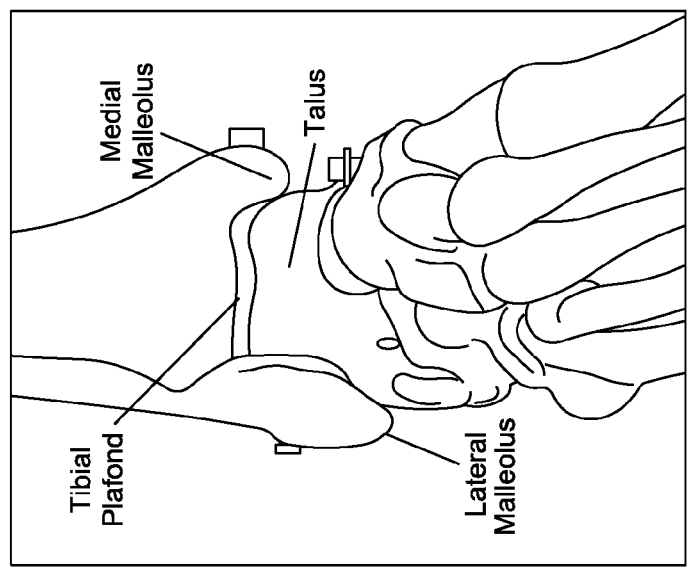
Figure 26:
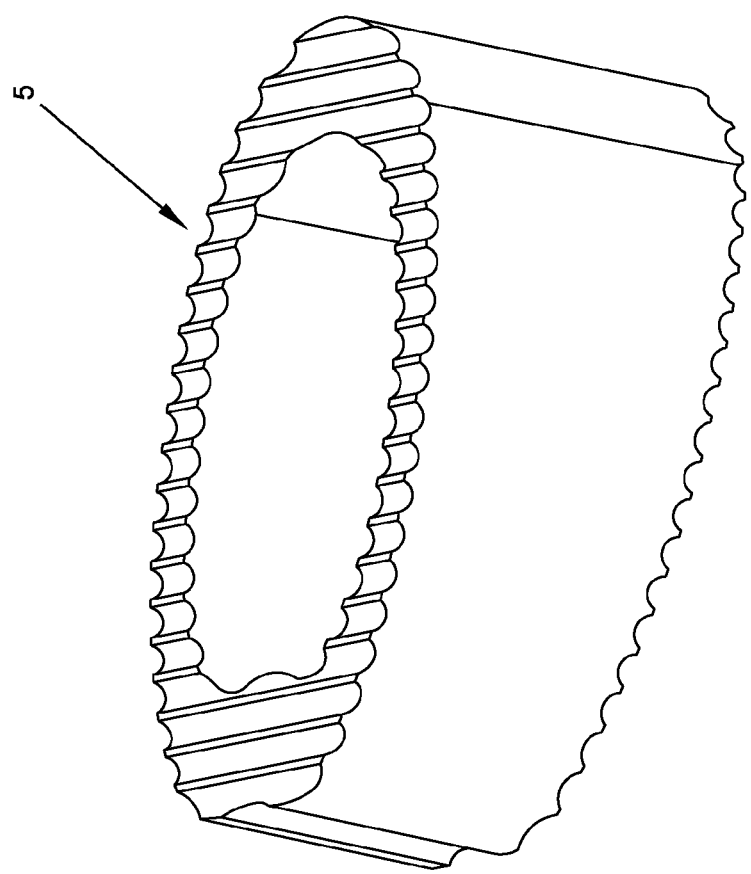
Figure 27:
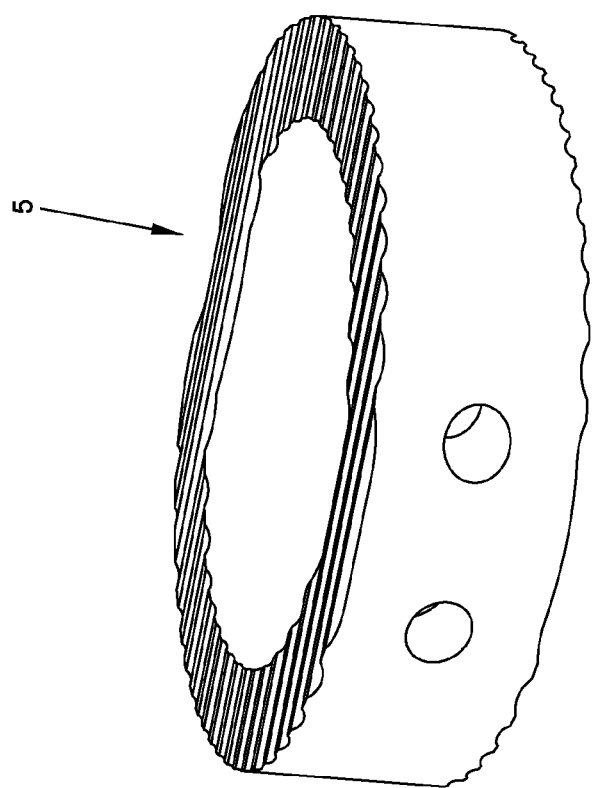
Figure 29:
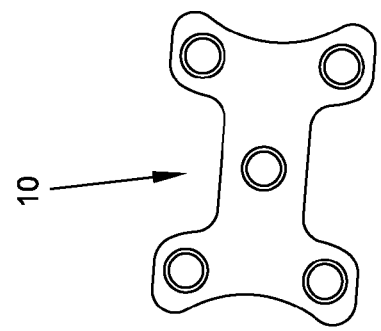
Figure 28:
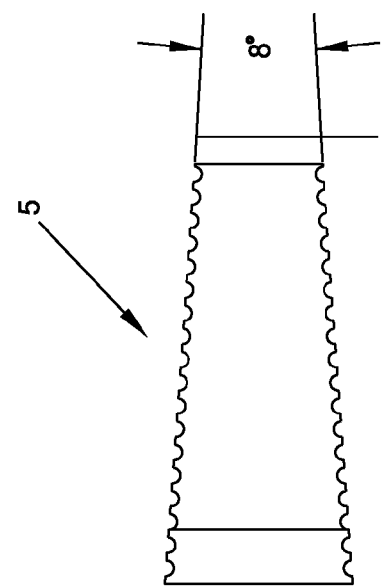
Figure 30:
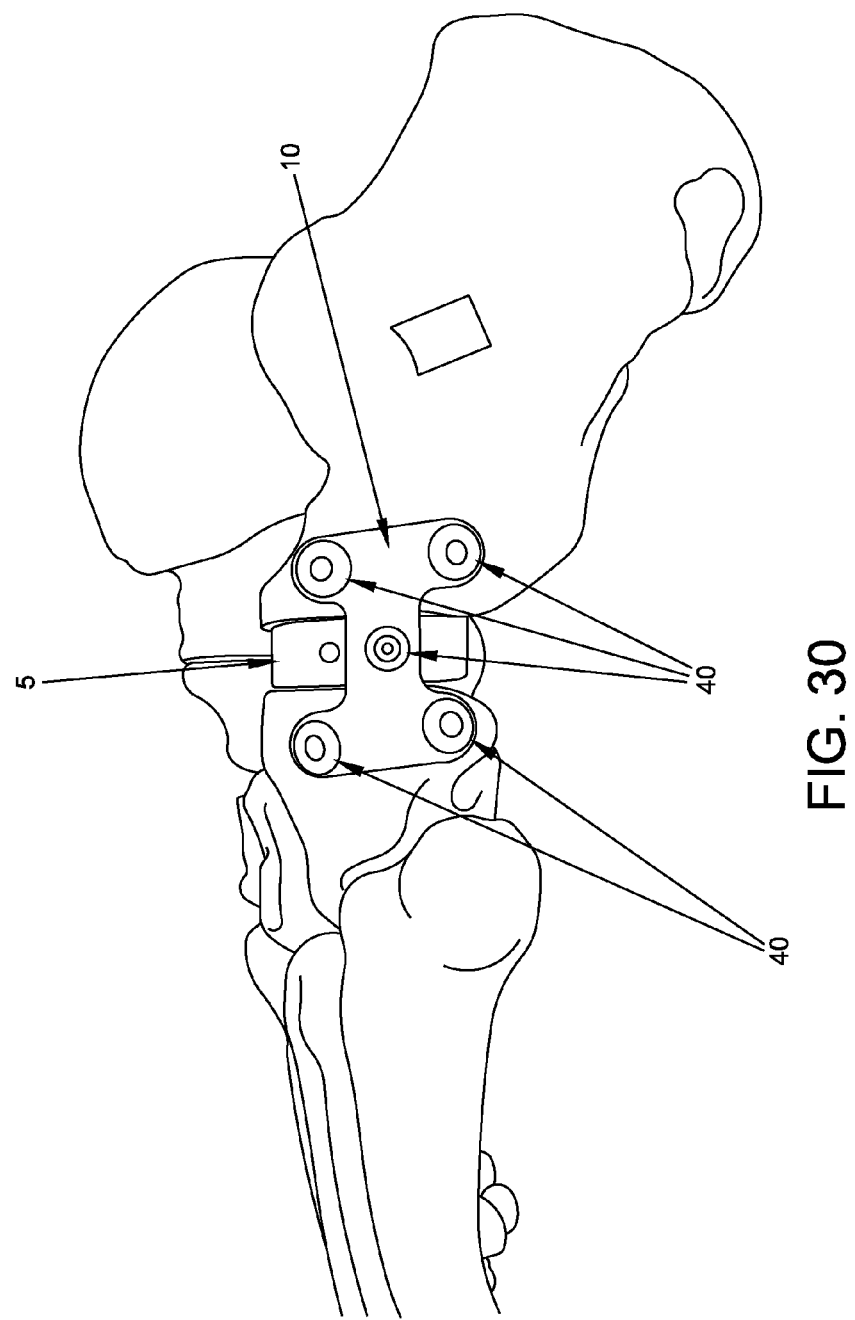

(iii) The Calcaneal Cuboid Bone Fusion (Lateral Column) (Wedge-Shaped) (PEEK) (Also Called The "Evans" And "Cotton" Procedure). This procedure involves arthrodesis of the calcaneal cuboid joint. The relevant anatomy is shown in FIGS. 23-25. In this bone fusion, the fusion block 5 shown in FIGS. 26-28 is used in conjunction with the fusion plate 10 shown in FIG. 29. As seen in FIG. 30, the fusion block 5 is interposed between the calcaneous bone and the cuboid bone, and then the fusion block is secured using fusion plate 10 and screws 40. Again, note how one of the screws 40 secures fusion plate 10 to fusion block 5 while others of the screws 40 secure fusion plate 10 to adjacent bone.

Figure 32:
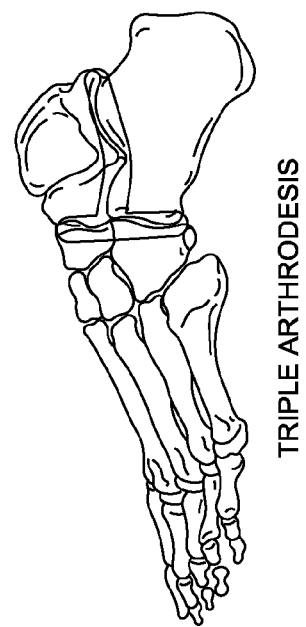
FIGS. 31-39 are schematic views showing an integrated talar/navicular bone fusion effected in accordance with the present invention.
Figure 31:
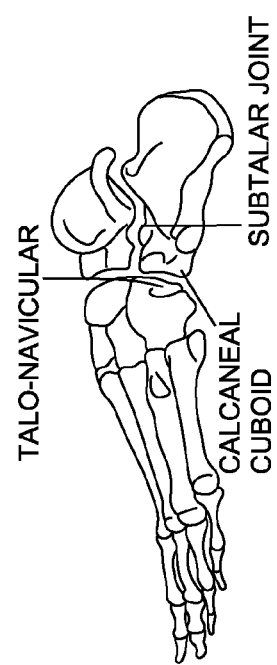
Figure 34:
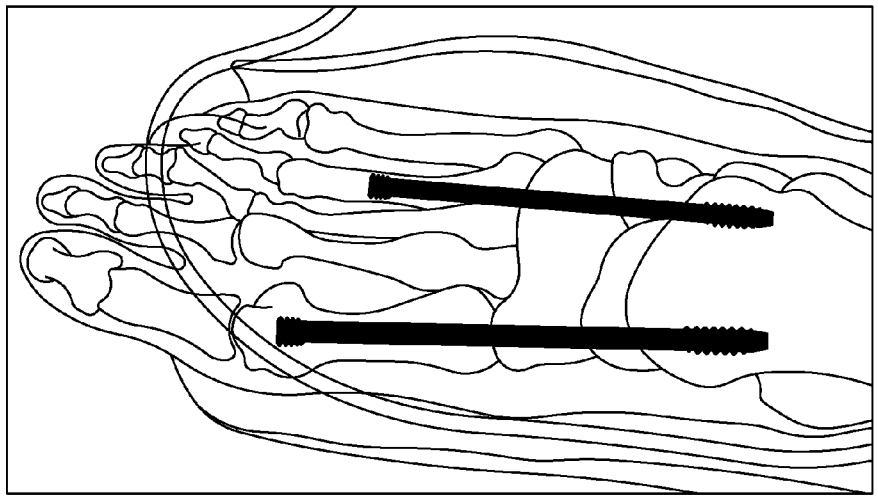
Figure 33:
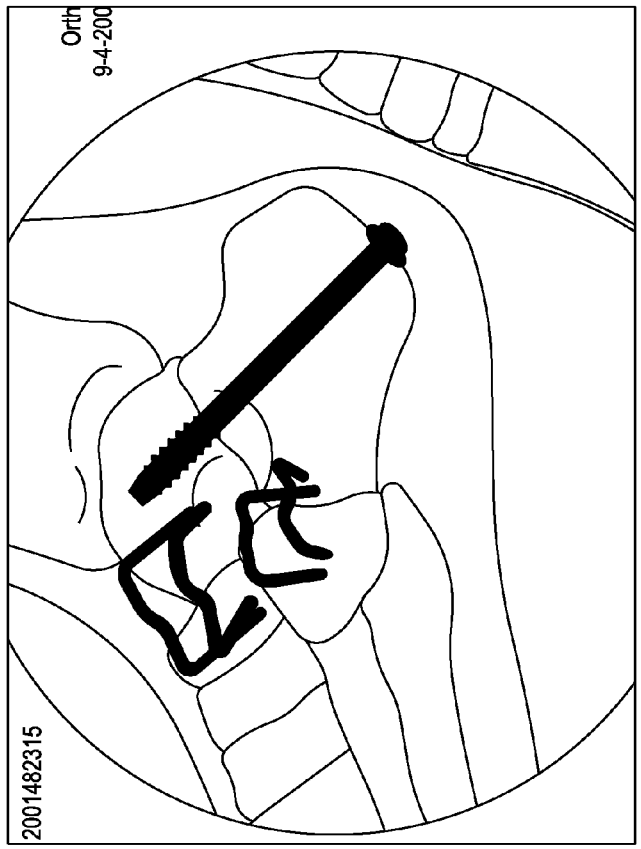
Figure 35:
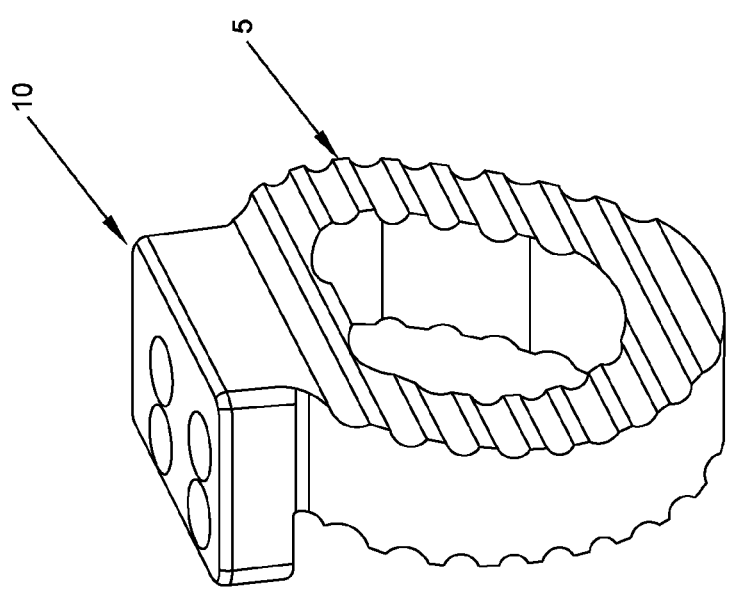
Figure 36:
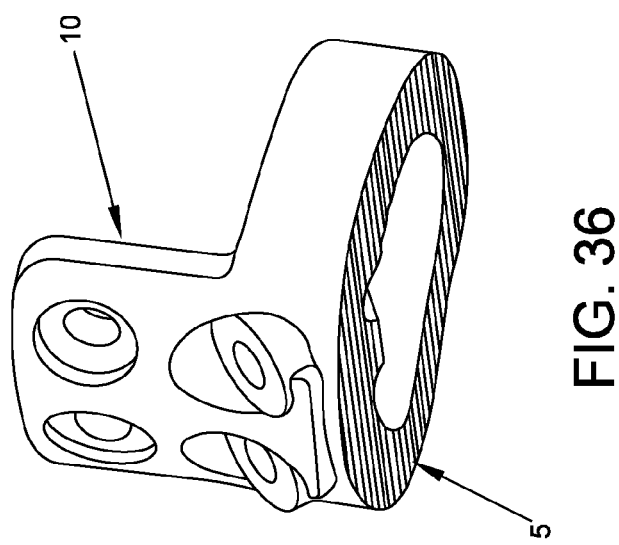
Figure 37:
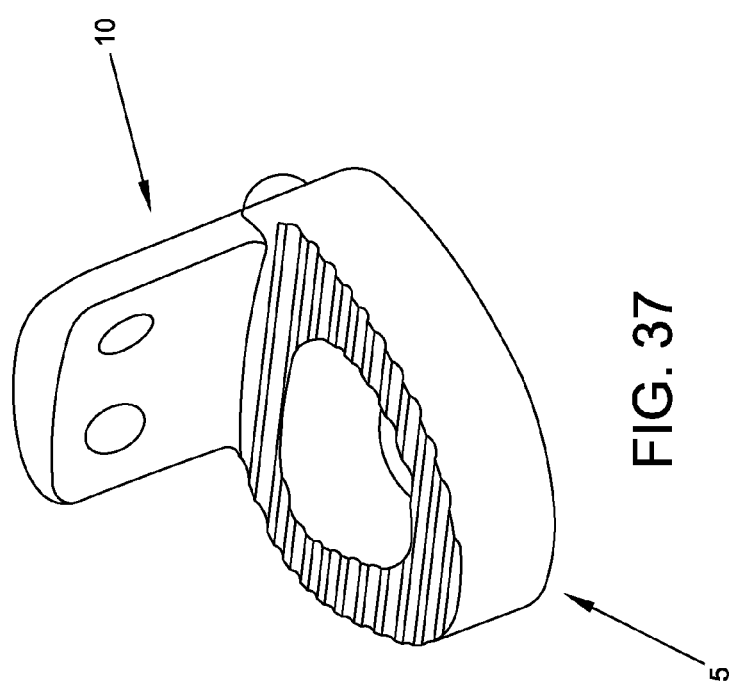
Figure 38:
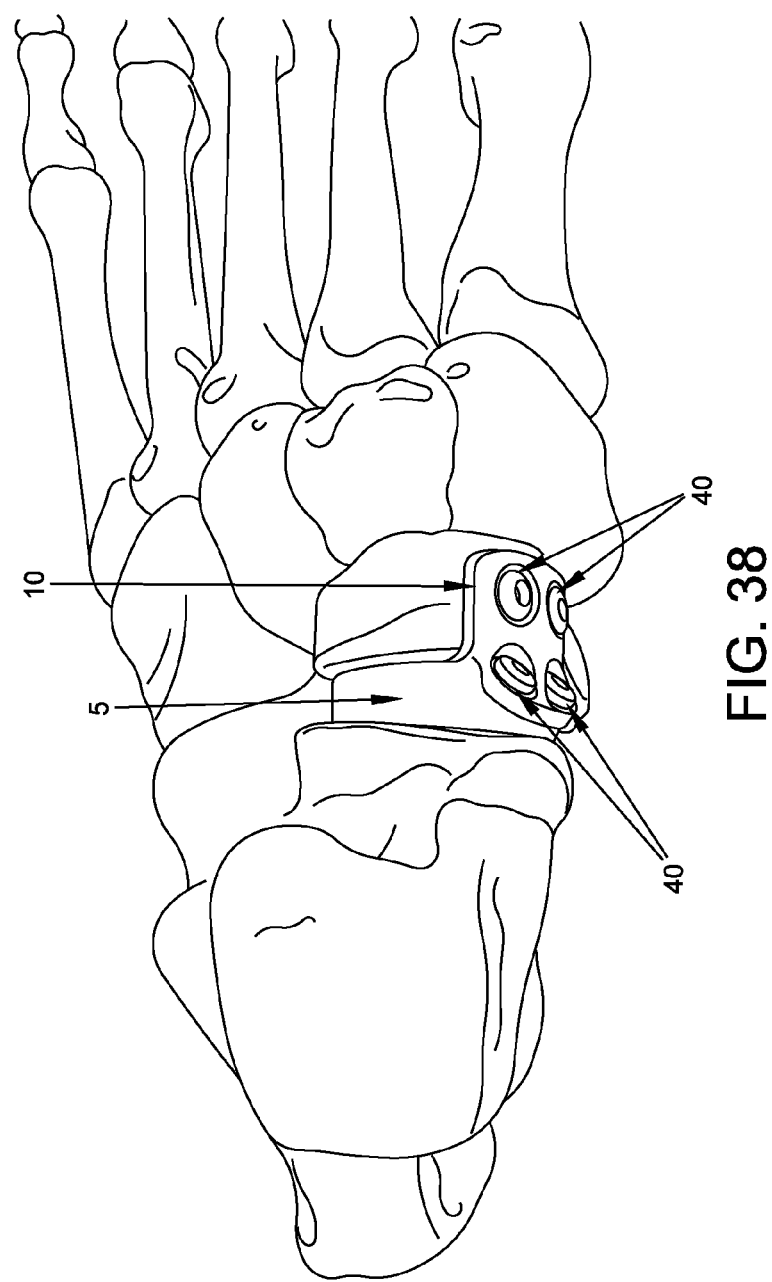
Figure 39:
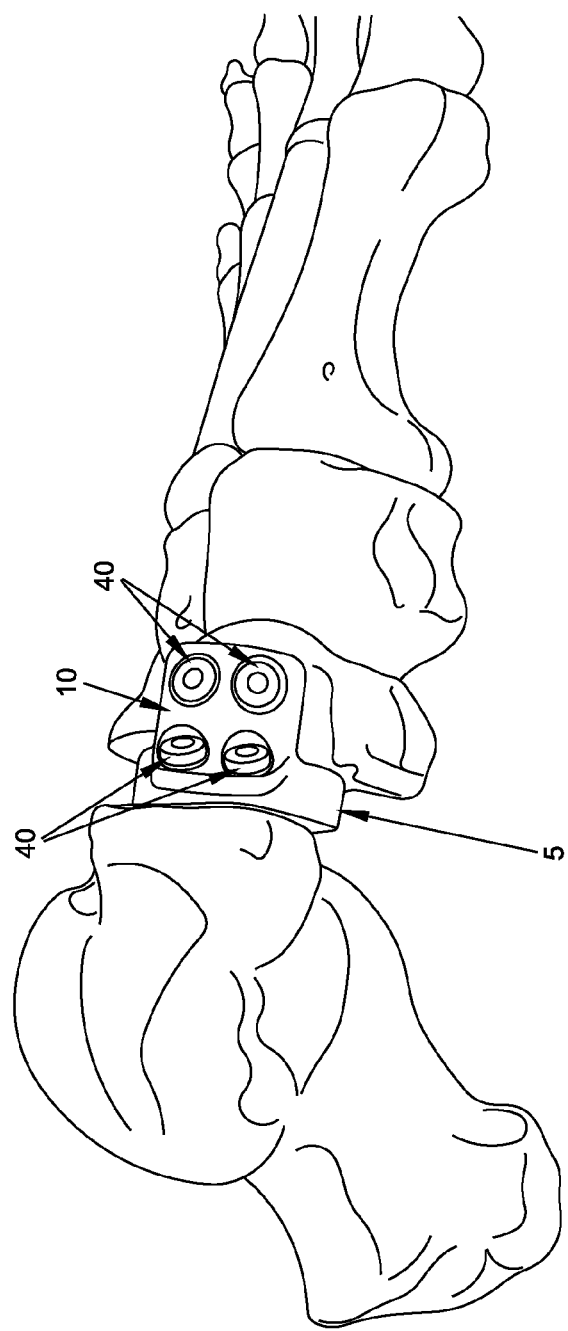

(iv) The Integrated Talar/Navicular Bone Fusion (PEEK). This procedure involves arthrodesis of the talar/navicular joint. The relevant anatomy is shown in FIGS. 31 and 32. A prior art bone fusion, using screws and staples, is shown in FIGS. 33 and 34. In a bone fusion effected using the present invention, a fusion block 5 having a fusion plate 10 formed integral therewith is used (see FIGS. 35-37). As seen in FIGS. 38 and 39, the fusion block 5 is interposed between the talar bone and the navicular bone, and then the fusion block is secured using fusion plate 10 and screws 40. Note how some of the screws 40 secure the implant to the talar bone while others of the screws 40 secure the implant to the navicular bone.

Figure 42:
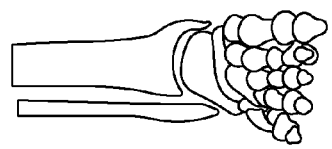
Figure 41:
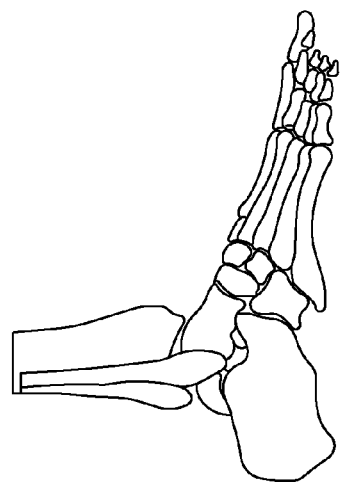
Figure 40:
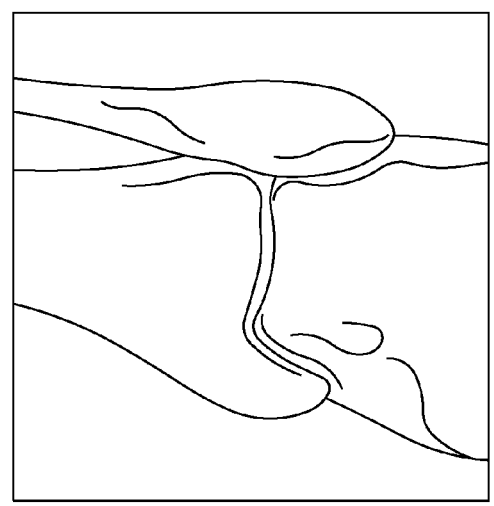
Figure 45:
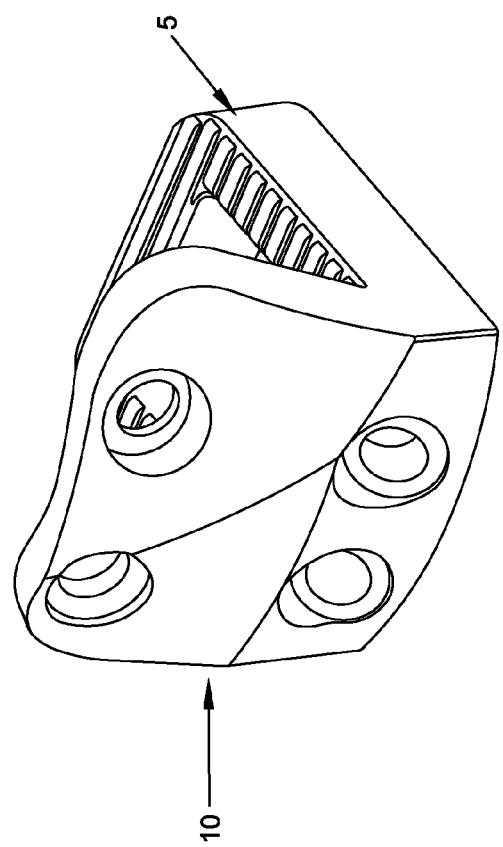
Figure 46:
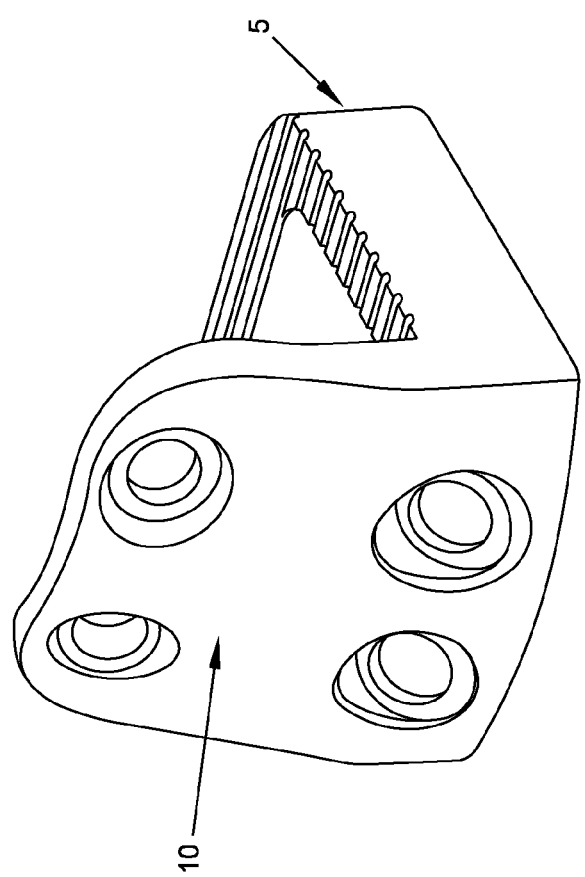
Figure 47:
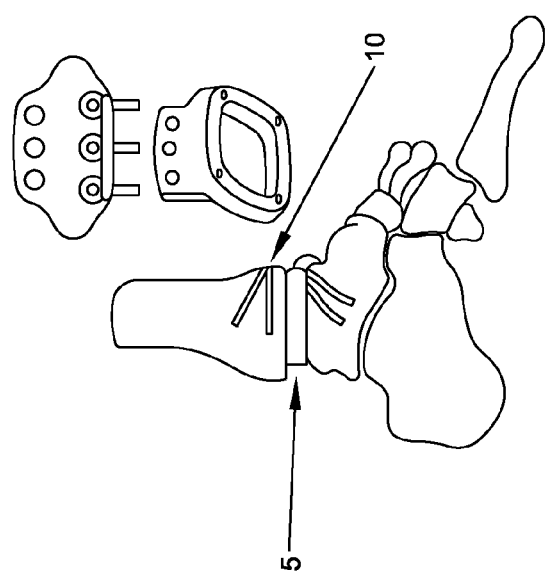
Figure 48:
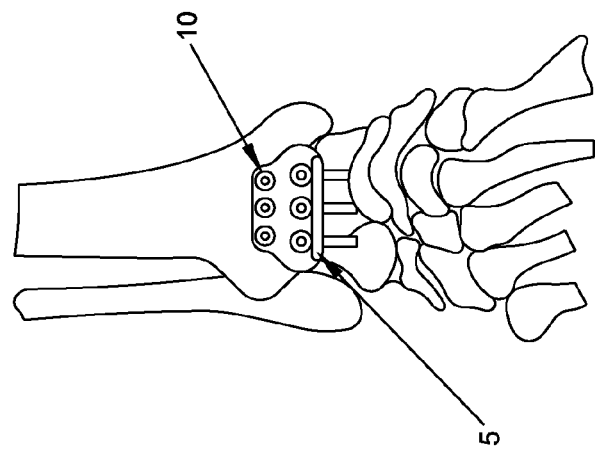
Figure 50:
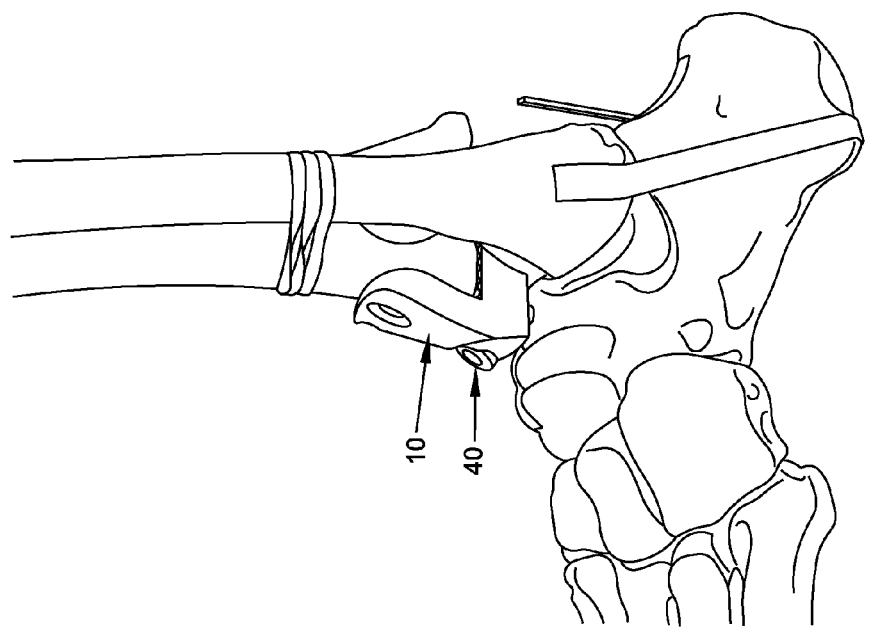
Figure 49:
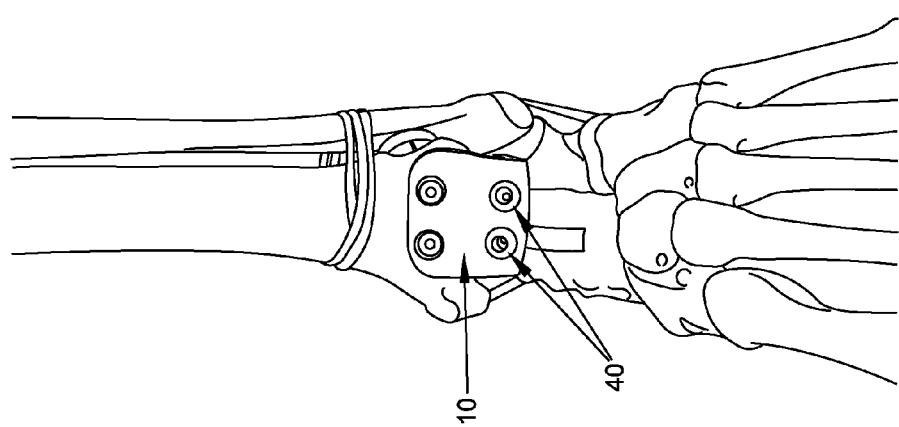

(v) Integrated Ankle Bone Fusion—(Ankle-Tibiotalar Joint) (Titanium). This procedure involves arthrodesis of the tibiotalar joint. The relevant anatomy is shown in FIGS. 40-42. In a bone fusion effected using the present invention, a fusion block 5 having a fusion plate 10 formed integral therewith is used (see FIGS. 43-46). As seen in FIGS. 47-50, the fusion block 5 is interposed between the tibia and the talar bone, and then the fusion block is secured using fusion plate 10 and screws 40. Note how some of the screws 40 secure the implant to the tibia while others of the screws 40 secure the implant to the talar bone.

Exemplary Procedures (i) Fusions of the Medial Column: Navicular Cuneiform Joint, First Metatarsal Cuneiform Joint.

The patient is placed supine with a contralateral bump under the hip to facilitate positional access, and the limb is placed under tourniquet. General or regional anesthesia can be used.

The incision is planned and made on the medial side of the foot approximately 3-4 cm over the joint which is to be fused. The skin and neurovascular bundle is gently retracted. Blunt and sharp dissection is carried deeply, taking care to ligate the communicating venous plexus as necessary. If the tibialis anterior attachment obscures access to the joint, the proximal and distal portions of the tendon expanse is tagged with suture and incised. To avoid retraction of the tendon proximally, an allise clamp can be used to hold the tendon in the surgical field. A linear incision of the periosteum is made. Using a key elevator, the periosteal structures are then bluntly raised dorsally and plantarly until the dorsal and plantar portions of the joint are easily visualized.

To facilitate joint resection, the dorsal and plantar ligaments of the joint which is to be fused are sharply released. Using an osteotome or saggital saw, the opposing joint surfaces (along with the subchondral plate) is resected. Using C-arm fluoroscopy, the joint resection is checked for remaining boney shelves and proper orientation. Further resections are performed as needed.

The size of the deficit is then measured by inserting trial sizing devices until the desired size is determined. An appropriately-sized implant is then selected from inventory and the fusion block is filled with bone graft material. Then the device is inserted into the deficit. The surrounding bone and the fusion block is then fixated with the fusion plates.

Appropriate fixation and apposition is determined by C-arm fluoroscopy. Then the surgical site is flushed with sterile saline. The deep structures are then closed with absorbable sutures and the tibialis tendon expanse is then reapproximated. The skin incision is closed and a posterior splint is applied as necessary.

(ii) Evans Osteotomy/Arthrodesis.

The patient is placed lateral side up, or with an ipsilateral bump under the hip to facilitate positional access, and the limb is placed under tourniquet. General or regional anesthesia can be used.

A curvilinear incision is planned and made on the lateral side of the foot approximately 2 cm proximal to the neck of the calcaneus and extending to the base of the fourth metatarsal. The skin and sural nerve is gently retracted. Blunt and sharp dissection is carried deeply, taking care to ligate the communicating venous plexus as necessary. The lateral border of the extensor digitorum brevis is identified. It is sharply dissected free from its proximal attachment over the superior border of the calcaneus. It is then reflected distally. An allise clamp can be used to hold the muscle away from the surgical field. A linear incision of the periosteum is made. Using a key elevator, the periosteal structures are then bluntly raised dorsally and plantarly until the dorsal and plantar portions of the bone(s) are easily visualized.

(iii) Evans Osteotomy.

If an osteotomy is to be performed, then the calcaneal ligaments should remain intact. A distraction device is then applied proximal and distal to the calcaneal neck. As an alternative, a Hintermann retractor can be applied. Using an osteotome or saggital saw, an osteotomy is performed from lateral to medial, taking care to perform the osteotomy at a right angle to the cortex. Once a complete osteotomy is achieved, the distraction device is engaged until the desired correction is achieved, taking care not to dorsally displace the distal calcaneal fragment. Proper sizing is then performed, and the implant (i.e., fusion block) is inserted into the joint which is to be fused. Then the implant is secured in place using one or more fusion plates and screws.

Appropriate fixation and apposition is determined by C-arm fluoroscopy. Then the surgical site is flushed with sterile saline. The deep structures are then closed with absorbable sutures, and the extensor digitorum brevis expanse is then reapproximated to its origin. The skin incision is closed and a posterior splint is applied as necessary.

(iv) Modified Evans Arthrodesis.

To facilitate joint resection, the dorsal and plantar ligaments of the calcaneal cuboid joint are sharply released. A distraction device is then applied to the central cuboid and the calcaneal neck. As an alternative, a Hintermann retractor can be applied.

Using an osteotome or saggital saw, the opposing joint surfaces (along with the subchondral plate) is resected. Using C-arm fluoroscopy, the joint resection is checked for remaining boney shelves and proper orientation. Further resections are performed as needed. The distraction device is engaged until the desired correction is achieved, taking care not to dorsally displace the cuboid. Proper sizing is then performed, and the implant (i.e., fusion block) is inserted into the joint which is to be fused. Then the implant is secured in place using one or more fusion plates and screws.

Appropriate fixation and apposition is determined by C-arm fluoroscopy. Then the surgical site is flushed with sterile saline. The deep structures are then closed with absorbable sutures, and the extensor digitorum brevis expanse is then reapproximated to its origin. The skin incision is closed and a posterior splint is applied as necessary.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for fusing a joint comprising a first bone having a first articulating cartilage surface supported by a first underlying bone structure comprising tubular cortical bone surrounding a core of cancellous bone, and a second bone having a second articulating cartilage surface supported by a second underlying bone structure comprising tubular cortical bone surrounding a core of cancellous bone, wherein the first articulating cartilage surface and the second articulating cartilage surface slidably engage one another at the joint, the method comprising:

resecting the first bone so as to remove the first articulating cartilage surface and a portion of the first underlying bone structure of the first bone so as to expose the tubular cortical bone and the core of cancellous bone of the remaining portion of the first underlying bone structure;

resecting the second bone so as to remove the second articulating cartilage surface and a portion of the second underlying bone structure of the second bone so as to expose the tubular cortical bone and the core of cancellous bone of the remaining portion of the second underlying bone structure;

inserting a fusion block between the resected first bone and the resected second bone, the fusion block comprising a hollow tubular structure characterized by a first end, a second end and a lumen extending from said first end to said second end, the fusion block being inserted between the resected first bone and the resected second bone so that the first end of the fusion block engages the tubular cortical bone of the remaining portion of the first underlying bone structure of the first bone and the second end of the fusion block engages the tubular cortical bone of the remaining portion of the second underlying bone structure of the second bone and so that the lumen of the fusion block provides a passageway connecting the core of the cancellous bone of the remaining portion of the first underlying bone structure and the core of the cancellous bone of the remaining portion of the second underlying bone structure, and inserting bone graft material into the lumen of the fusion block so that the bone graft material extends from the core of the cancellous bone of the remaining portion of the first underlying bone structure and the core of the cancellous bone of the remaining portion of the second underlying bone structure; and securing the fusion block to the resected first bone and the resected second bone using at least one fusion plate.

2. A method according to claim 1 wherein the bone graft material is inserted into the lumen of the fusion block before the fusion block is inserted between the resected first bone and the resected second bone.

3. A method according to claim 1 wherein the bone graft material is inserted into the lumen of the fusion block after the fusion block is inserted between the resected first bone and the resected second bone.

4. A method according to claim 1 wherein the fusion plate is formed integral with the fusion block.

5. A method according to claim 1 wherein the fusion plate is formed separate from the fusion block.

6. A method according to claim 5 wherein the fusion plate is secured to the fusion block prior to insertion of the fusion block between the resected first bone and the resected second bone.

7. A method according to claim 5 wherein the fusion plate is secured to the fusion block after insertion of the fusion block between the resected first bone and the resected second bone.

8. A method according to claim 1 wherein the apparatus comprises two fusion plates.

9. A method according to claim 8 wherein the first fusion plate is configured to be attached to the resected first bone and the second fusion plate is configured to be attached to the resected second bone.

10. A method according to claim 9 wherein the first fusion plate is formed integral with the fusion block.

11. A method according to claim 9 wherein the second fusion plate is formed separate from the fusion block.

\* \* \* \* \*